(12) United States Patent
Fung et al.

(10) Patent No.: US 7,674,459 B2
(45) Date of Patent: Mar. 9, 2010

(54) TREATMENT OF CANCER WITH A NOVEL ANTI-IL13 MONOCLONAL ANTIBODY

(75) Inventors: Sek Chung Fung, Gaithersburg, MD (US); Matthew Moyle, Redmond, WA (US)

(73) Assignee: Genentech, Inc., South San Francisco, CA (US)

( * ) Notice: Subject to any disclaimer, the term of this patent is extended or adjusted under 35 U.S.C. 154(b) by 157 days.

(21) Appl. No.: 10/583,926

(22) PCT Filed: Dec. 23, 2004

(86) PCT No.: PCT/US2004/043541

§ 371 (c)(1),
(2), (4) Date: Jun. 20, 2007

(87) PCT Pub. No.: WO2005/062972

PCT Pub. Date: Jul. 14, 2005

(65) Prior Publication Data

US 2008/0008648 A1 Jan. 10, 2008

Related U.S. Application Data

(60) Provisional application No. 60/532,130, filed on Dec. 23, 2003.

(51) Int. Cl.
*A61K 39/395* (2006.01)

(52) U.S. Cl. .................................................. 424/130.1

(58) Field of Classification Search ........................ None
See application file for complete search history.

(56) References Cited

U.S. PATENT DOCUMENTS

| | | | |
|---|---|---|---|
| 5,011,778 | A | 4/1991 | Newman et al. |
| 5,359,037 | A | 10/1994 | Wallach et al. |
| 5,596,072 | A | 1/1997 | Culpepper et al. |
| 5,677,165 | A | 10/1997 | De Boer et al. |
| 5,705,154 | A | 1/1998 | Dalie et al. |
| 5,710,023 | A | 1/1998 | Collins et al. |
| 5,717,072 | A | 2/1998 | Mosley et al. |
| 5,747,037 | A | 5/1998 | Noelle et al. |
| 5,783,181 | A | 7/1998 | Browne et al. |
| 6,156,321 | A | 12/2000 | Thorpe et al. |
| 6,468,528 | B1 | 10/2002 | Mak et al. |
| 6,911,530 | B1 | 6/2005 | Willson et al. |
| 7,078,494 | B1 | 7/2006 | Collins et al. |
| 7,078,496 | B2 | 7/2006 | Collins et al. |
| 7,312,024 | B2 | 12/2007 | Mak et al. |
| 2003/0049257 | A1 | 3/2003 | Mak et al. |
| 2005/0277126 | A1 | 12/2005 | Collins et al. |
| 2008/0008648 | A1 | 1/2008 | Fung et al. |

FOREIGN PATENT DOCUMENTS

| | | |
|---|---|---|
| EP | 1 270 595 A1 | 1/2003 |
| EP | 1 327 681 A1 | 7/2003 |
| EP | 1 646 656 A2 | 1/2005 |
| WO | WO 89/04838 | 6/1989 |
| WO | WO 91/09059 | 6/1991 |
| WO | WO 93/15766 | 8/1993 |
| WO | WO 94/04680 | 3/1994 |
| WO | WO 94/14975 | 7/1994 |
| WO | WO 95/14780 | 6/1995 |
| WO | WO 97/15663 | 5/1997 |
| WO | WO 97/29131 | 8/1997 |
| WO | WO 97/31946 | 9/1997 |
| WO | WO 97/47742 | 12/1997 |
| WO | WO 98/10638 | 3/1998 |
| WO | WO 98/30240 | 7/1998 |
| WO | WO 00/15663 | 3/2000 |
| WO | WO 00/36103 | 6/2000 |
| WO | WO 02/055100 | 7/2002 |
| WO | WO 03/018635 | 3/2003 |
| WO | WO 2005/007699 A2 | 1/2005 |
| WO | WO 2005/062967 A2 | 7/2005 |
| WO | WO 2005/062972 A2 | 7/2005 |
| WO | WO 2008/140455 A1 | 11/2008 |

OTHER PUBLICATIONS

U.S. Appl. No. 10/583,927, filed Dec. 23, 2004, Fung et al.
U.S. Appl. No. 12/240,604, filed Dec. 29, 2008, Fung et al.
Andrews et al., 2002, "Kinetic analysis of the interleukin-13 receptor complex," J. Biol. Chem., vol. 277(48):46073-46078.
Bellanti, 1998, "Cytokines and allergic diseases: Clinical aspects," Allergy and Asthma, Proc., vol. 19(6):337-340.
Blanchard et al., 2005, "Inhibition of human interleukin-13-induced respiratory and oesophageal inflammation by anti-human-interleukin-13 antibody (CAT-354)," Clin. Exp. Allergy, vol. 35:1096-1103.
Bost et al., 1996, "In vivo treatment with anti-interleukin-13 antibodies significantly reduces the humoral immune response against an oral immunogen in mice," Immunology, vol. 87(4):633-641.
Bree et al., 2007, "IL-13 blockade reduces lung inflammation after Ascaris suum challenge in cynomolgus monkeys," J. Allergy Clin. Immunol., vol. 119(5)1251-1257.
Brinkmann et al., 1995, "TCR-stimulated naive human $CD4^+45R0^-$ T cells develop into effector cells that secrete IL-13, IL-5, and IFN-$\gamma$, but no IL-4, and help efficient IgE production by B cells," J. Immunol., vol. 154(7):3078-3087.
Campbell et al., 2003, "Allergic humans are hypo-responsive to CXCR3 chemokines in a Th1 immunity-promoting loop," FASEB J., vol. 18(2):329-331.
Caput et al., 1996, "Cloning and characterization of a specific interleukin (IL)-13 binding protein structurally related to the IL-5 receptor $\alpha$ chain," J. Biol. Chem., vol. 271(28):16921-16926.
Carballido et al., 1995, "IL-4 induces human B cell maturation and IgE synthesis in SCID-hu mice," J. Immunol., vol. 155(9):4162-4170.
Casolaro et al., 1996, "Biology and genetics of atopic disease," Curr. Opin. Immunol., vol. 8:796-803.

(Continued)

*Primary Examiner*—Christopher H Yaen
(74) *Attorney, Agent, or Firm*—Jones Day

(57) ABSTRACT

The present invention relates to the treatment of IL13 dependent neoplastic disorders comprising the administration of novel anti-IL13 antibodies, The invention also includes diagnosing such tumors or cancer using the antibodies of the present invention to detect overexpression of IL13 in the patient.

30 Claims, 9 Drawing Sheets

OTHER PUBLICATIONS

De Vries et al., 1996, "Modulation of the human IgE response," Eur. Respir. J., Suppl. 22:58s-62s.

De Vries, 1994, "Novel fundamental approaches to intervening in IgE-mediated allergic diseases," J. Invest. Dematol., vol. 102:141-144.

Debinski et al., 1995, "A novel chimeric protein composed on interleukin 13 and pseudomonas exotoxin is highly cytotoxic to human carcinoma cells expressing receptors for interleukin 13 and interleukin 4," J. of Biological Chemistry, vol. 270(28):16775-16780.

Debinski et al., 1995, "Human glioma cells overexpress receptors for interleukin 13 and are extremely sensitivity to a novel chimeric protein composed of interleukin 13 and pseudomonas exotoxin," Clinical Cancer Research, vol. 1:1253-258.

Donaldson et al., 1998, "The murine IL-13 receptor alpha 2: molecular cloning, characterization, and comparison with murine IL-13 receptor alpha 1," J. Immunol., vol. 161:2317-2324.

Doucet et al., 1998, "Interleukin (IL) 4 and IL-13 act on human lung fibroblasts," J. Clin. Invest., vol. 101:2129-2139.

Enomoto et al., 2002, "High-throughput miniaturized immunoassay for human interleukin-13 secreted from NK3.3 cells using homogenous time-resolved fluorescence," J of Pharm and Biomedical Analysis, vol. 28:73-79.

Fichtner-Feigl et al., 2005, "IL-13 signaling through the IL-13$\alpha_2$ receptor is involved in induction of TGF-$\beta_1$ production and fibrosis," Nature Medicine, vol. 12: 99-106.

Gabrielsson et al., 1998, "Increased frequencies of allergen-induced interleukin-13 producing cells in atopic individuals during the pollen season," Scand. J. Immunol., vol. 48:429-435.

Ghaffar et al., 1997, "IL-13 mRNA and immunoreactivity in allergen-induced rhinitis: Comparison with IL-4 expression and modulation by topical glucocorticoid therapy," Am. J. Respir. Cell Mol. Biol., vol. 17:17-24.

Ghamdi et al., 1997, "IL-4 and IL-3 expression in chronic sinusitis: Relationship with cellular infiltrate and effect of topical corticosteroid treatment," J. of Otolaryngology, vol. 26(3):160-166.

Grünig et al., 1998, "Requirement for IL-13 independently of IL-4 in experimental asthma," Science, vol. 282:2261-2263.

Hamid et al., 1996, "In vivo expression of IL-12 and IL-13 in atopic dermatitis," J. Allergy Clin. Immunol., vol. 98:225-231.

Huang et al., 1995, "IL-13 expression at the sites of allergen challenge in patients with asthma," J. Immunol., vol. 155:2688-2694.

Humbert et al., 1997, "Elevated expression of messenger ribonucleic acid encoding IL-13 in the bronchial mucosa of atopic and nonatopic subjects with asthma," J. Allergy Clin. Immunol., vol. 99:657-665.

Kapp et al., 1999, "Interleukin 13 is secreted by and stimulated the growth of Hodgkin and Reed-Sternberg Cells," J. Exp. Med., vol. l89(12):1939-1945.

Kasaian et al., 2007, "Efficacy of IL-13 neutralization in a sheep model of experimental asthma," Am. J. Respir. Cell Mol. Biol., vol. 36:368-376.

Kawakami et al., 2001, "Interleukin-13 receptor-targeted cancer therapy in an immunodeficient animal model of human head and neck cancer," Cancer Research, vol. 61:6194-6200.

Kimata et al., 1995, "Involvement of interleukin (IL)-13, but not IL-4, in spontaneous IgE and IgG4 production in nephritic syndrome," Eur. J. Immunol., vol. 25:1497-1501.

Kotsimbos et al., 1996, "Interleukin-13 and interleukin-4 are coexpressed in atopic asthma," Proceedings of the Assoc. of American Physicians, vol. 108(5):368-373.

Kroegel et at, 1996, "Endobronchial secretion of interleukin-13 following local allergen challenge in atopic asthma: relationship to interleukin-4 and eosinophil counts," Eur. Respir. J., vol. 9:899-904.

Levy et al., 1997, "Role of IL-13 in CD4 T cell-dependent IgE production in atopy," Int. Arch. Allergy Immunol., vol. 112:49-58.

Maini et al., 1997, "Interleukin-13 receptors on human prostate carcinoma cell lines represent a novel target for a chimeric protein composed of IL-13 and a mutated form of pseudomonas exotoxin," J. Urology, vol. 158:948-953.

Marsh et al., 1994, "Linkage analysis of IL4 and other chromosome 5q31.1 markers and total serum immunoglobulin E concentrations," Science, vol. 264:1152-1156.

McKenzie et al., 1993, "Interleukin 13, a T-cell-derived cytokine that regulates human monocyte and B-cell function," Proc. Natl. Acad. Sci. U.S.A., vol. 90(8):3735-3739.

McKenzie et al., 1994, "Measurement of interleukin-13," Current Protocols in Immunology, Unit 6.18, Suppl. 10:6.18.1-6.18.5, Coligan et al. eds., John Wiley & Sons, New York.

McKenzie et al., 1998, "Impaired development of Th2 cells in IL-13 deficient mice," Immunity, vol. 9:423-432.

Mentink-Kane et al ., 2004, "Opposing roles for IL-13 and IL-13 receptor a2 in health and disease," Immunological Reviews, vol. 202:191-202.

Naseer et al., 1997, "Expression of IL-12 and IL-13 mRNA in asthma and their modulation in response to steroid therapy," Am. J. Respir. Crit. Care Med., vol. 155:845-851.

Ohno et al., 1985, "Antigen-binding specificities of antibodies are primarily determined by seven residues of VH," Proc. Natl. Acad. Sci. U S A., vol. 82(9):2945-2949.

Oshima et al., 2001, "Characterization of a powerful high affinity antagonist that inhibits biological activities of human interleukin-13," J. Biol. Chem., vol. 276(18):15185-15191.

Pawankar et al., 1997, "Nasal mast cells in perennial allergic rhinitics exhibit increased expression of the FœRI, CDR40L, IL-4, and IL-13, and can induce IgE synthesis in B cells," J. Clin. Invest., vol. 99(7):1492-1499.

Postma et al., 1995, "Genetic susceptibility to asthma—Bronchial hyperresponsiveness coinherited with a major gene for atopy," N. Engl. J. Med., vol. 333(14):894-900.

Punnonen et al., "Cytokines and IgE regulation," Allergy and Allergic Diseases: The New Mechanisms and Therapeutics, pp. 13-40, Edited by J.A. Denburg, Human Press Inc., Totowa, NJ 1998.

Roitt et al., 1996, Immunology, Fourth Edition, Published by Mosby, London, pp. 22-1-22.5 and glossary.

Roitt, I.M., 1988, Essential Immunology, Sixth Edition, Blackwell Scientific Publications, Oxford, pp. 195-196.

Schildbach et al., 1993, "Modulation of antibody affinity by a non-contact residue," Protein Sci. vol. 2(2):206-14.

Skinnider et al., 2002, "Signal transducer and activator of transcription 6 is frequently activated in Hodgkin and Reed-Sternberg cells of Hodgkin lymphoma," Blood, vol. 99(2):618-626.

Skinnider et al., 2002, "The role of interleukin 13 in classical Hodgkin lymphoma," Leuk. Lymphoma, vol. 43(6):1203-1210.

Tekkanat et al., 2001, "IL-13-induced airway hyperreactivity during respiratory syncytial virus infection is STAT6 dependent," J. Immunol., vol. 166:3542-3548.

Terabe et al., 2000, "NKT cell-mediated repression of tumor immunosurveillance by IL-13 and the IL-4R-STAT6 pathway," Nat. Immunol., vol. 1(6):515-520.

Terabe et al., 2004, "Role of IL-13 in regulation of anti-tumor immunity and tumor growth," Cancer Immunol. Immunother., vol. 53:79-85.

Trieu et al., "Inhibition of Hodgkin lymphoma cell line growth using an adenovirus expressing the soluble IL-13 decoy receptor (sIL-13Ralpha2)," Blood vol. 100(11):Abstract No. 2272 & 44 Annual meeting of the American Society of Hematology; Philadelphia, PA, USA, Dec. 6-10, 2002.

Trieu et al., 2004, "Soluble interleukin-13R$\alpha$2 decoy receptor inhibits Hodgkin's lymphoma growth in vitro and in vivo," Cancer Research, vol. 64:3271-3275.

Van Der Pouw Kraan et al., 1998, "The role of IL-13 in IgE synthesis by allergic asthma patients," Clin. Exp. Immunol., vol. 111:129-135.

Van Der Pouw Kraan et al., 1996, "Human IL-13 production is negatively influenced by CD3 engagement—enhancement of IL-13 production by cyclosporine A," J. Immunol., vol. 156(5):1818-1823.

Vugmeyster et al., 2008, "Preclinical pharmacokenetics, interspecies scaling, and tissue distribution of humanized monoclonal anti-IL-13 antibodies with different IL-13 neutralization mechanisms," Intl. Immunopharmacol., vol. 8:477-483.

Warner, 1998, "Bronchial hyperresponsivenes, atopy, airway inflammation, and asthma," Pediatr. Allergy Immunol., vol. 9:56-60.

Wills-Karp et al., 1998, "Interleukin-13: central mediator of allergic asthma," Science, vol. 282:2258-2261.

Wynn, T. A., 2003, "IL-13 effector functions," Annual Review of Immunol., vol. 21:425-456.

Yang et al., 2004, "Anti-IL-13 monoclonal antibody inhibits airway hyperresponsiveness, inflammation and airway remodeling," Cytokine, vol. 28:224-232.

Yang et al., 2005, "Therapeutic dosing with anti-interleukin-13 monoclonal antibody inhibits asthma progression in mice," J. Pharmacol. Exp. Ther., vol. 312:8-15.

Yssel et al., 1998, "The role of IgE in asthma," Clin. Exp. Allergy, vol. 28, Supp. 5:104-109.

Zhang et al., 2003, "Identification of monoclonal antibodies against IL-6," Molecular Cardiology of China, vol. 3(3):152-156.

Roitt et al., Immunology, 2000, Publisher "Mir", Moscow, pp. 110-111.

Fig. 1 Binding of anti-IL13 mAbs to human IL-13 in ELISA

Fig. 2 Binding of anti-IL13 mAbs to MT-IL13/Fc

Fig. 3 Anti-IL13 mAb JES10-5A2 does not compete with the binding of mAb 228B/C-1-HRP to Human IL-13 in ELISA Fig. 4 Effect of anti-IL13 mAbs on the proliferation of L-1236 cells Fig. 5 Effect of anti-IL13 mAbs on IL13-induced suppression of CD14 expression in human monocytes Fig. 6 Effect of anti-IL13 mAbs on IL13-induced upregulation of CD23 expression in human monocytes Fig. 7 Anti-IL13 mAbs Inhibit IL13-Induced Stat6 Phosphorylation in THP-1 Cells

Figure 8
Anti-IL13 228B/C-1 Vk:

NIVLTQSPASLAVSLGQRATISC RASKSVDSYGNSFMH W
YQQKPGQPPKLLIY LASNLES GVPARFSGSGSRTDFTL
TIDPVEADDAASYYC QQNNEDPRT FGGGTKLEIKRA (SEQ ID NO 3)

Anti-IL13 228B/C-1 Vh:

QVQLQESGPGLVAPSQSLSITCTVSGFSLN AYSVNWVRQ
PPGKGLEWLG MIWGDGKIVYNSALKSRLNISKDSSKSQV
FLKMSSLQSDDTARYYCA GDGYYPYAMDNWGHGTSVTV
SS (SEQ ID NO 4)

FIGURE 9: Variable Region Amino Acid Sequences for certain anti-IL13 Candidates:

CL-89 Vk (SEQ ID NO: 142):

DIVMTQSPDSLSVSLGERATINCRASKSVDSYGNSFMHWYQQKPGQPPKLLIYLASNLESGVPDRFSGSGSGT
DFTLTISSLQAEDVAVYYCQQNEDPRIFGGGTKVEIKR

CL-276G Vh (SEQ ID NO 143):

QVTLRESGPALVKPTQTLTLTCTVSGFSLSAYSVNWIRQPPGKALEWLAMIWGDGKIVYNSALKSRLTISKDTS
KNQVVLTMTNMDPVDTATYYCAGDGYYPYAMDNWGQGSLVTVSS

RL-36 (Random Library Candidate) Vk (SEQ ID NO 144):

DIVMTQSPDSLSVSLGERATINCRASKSVDSYGNSFMHWYQQKPGQPPKLLIYLASNLESGVPDRFSGSGSGT
DFTLTISSLQAEDVAVYYCQQNEDPRIFGGGTKVEIKR

RL-36 (Random Library Candidate) Vh (SEQ ID NO 145):

QVTLRESGPALVKPTQTLTLTCTGSGFSLSAYSVNWIRQPPGKALEWLAMIWGDGKIVYNSALKSRLTISKDTS
KNQVVLTMTNMDPVDTATYYCAVDGYYPAMDNWGQGSLVTV

RL36-L1.59 (L1 Affinity Matured Candidate) Vk (SEQ ID NO 150):

DIVMTQSPDSLSVSLGERATINCRASKSVDSYGQSFMHWYQQKPGQPPKLLIYLASNLESGVPDRFSGSGSGT
DFTLTISSLQAEDVAVYYCQQNEDPRIFGGGTKVEIKR

RL36-L1.59 (L1 Affinity Matured Candidate) Vh (SEQ ID NO 151):

QVTLRESGPALVKPTQTLTLTCTGSGFSLSAYSVNWIRQPPGKALEWLAMIWGDGKIVYNSALKSRLTISKDTS
KNQVVLTMTNMDPVDTATYYCAVDGYYPYAMDNWGQGSLVTVSS
SS

SEQUENCE LISTING

<160> NUMBER OF SEQ ID NOS: 152

<210> SEQ ID NO 1
<211> LENGTH: 114
<212> TYPE: PRT
<213> ORGANISM: Homo sapiens

<400> SEQUENCE: 1

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln

```
                65                  70                  75                  80
Phe Ser Ser Leu His Val Arg Asp Thr Lys Ile Glu Val Ala Gln Phe
                    85                  90                  95
Val Lys Asp Leu Leu Leu His Leu Lys Lys Leu Phe Arg Glu Gly Arg
                100                 105                 110
Phe Asn

<210> SEQ ID NO 2
<211> LENGTH: 114
<212> TYPE: PRT
<213> ORGANISM: Homo sapiens
<220> FEATURE:
<221> NAME/KEY: misc_feature
<222> LOCATION: (13)..(13)
<223> OTHER INFORMATION: Xaa can be any naturally occurring amino acid

<400> SEQUENCE: 2

Ser Pro Gly Pro Val Pro Ser Thr Ala Leu Arg Xaa Leu Ile Glu
1               5                   10                  15

Glu Leu Val Asn Ile Thr Gln Asn Gln Lys Ala Pro Leu Cys Asn Gly
                20                  25                  30

Ser Met Val Trp Ser Ile Asn Leu Thr Ala Gly Met Tyr Cys Ala Ala
            35                  40                  45

Leu Glu Ser Leu Ile Asn Val Ser Gly Cys Ser Ala Ile Glu Lys Thr
        50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                    85                  90                  95

Val Lys Asp Leu Leu Leu His Leu Lys Lys Leu Phe Arg Glu Gly Arg
                100                 105                 110

Phe Asn

<210> SEQ ID NO 3
<211> LENGTH: 113
<212> TYPE: PRT
<213> ORGANISM: Murinae gen. sp.
<220> FEATURE:
<221> NAME/KEY: CHAIN
<222> LOCATION: (1)..(113)
<223> OTHER INFORMATION: VARIABLE REGION OF LIGHT CHAIN OF MONOCLONAL
      ANTIBODY 228B/C

<400> SEQUENCE: 3

Asn Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Ser Tyr Tyr Cys Gln Gln Asn Asn
                    85                  90                  95

Glu Asp Pro Arg Thr Phe Gly Gly Gly Thr Lys Leu Glu Ile Lys Arg
                100                 105                 110
```

Ala

<210> SEQ ID NO 4
<211> LENGTH: 118
<212> TYPE: PRT
<213> ORGANISM: Murinae gen. sp.
<220> FEATURE:
<221> NAME/KEY: CHAIN
<222> LOCATION: (1)..(118)
<223> OTHER INFORMATION: VARIABLE REGION OF HEAVY CHAIN OF MONOCLONAL
      ANTIBODY 228B/C

<400> SEQUENCE: 4

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Asn Ala Tyr
            20                  25                  30

Ser Val Asn Trp Val Arg Gln Pro Pro Gly Lys Gly Leu Glu Trp Leu
        35                  40                  45

Gly Met Ile Trp Gly Asp Gly Lys Ile Val Tyr Asn Ser Ala Leu Lys
    50                  55                  60

Ser Arg Leu Asn Ile Ser Lys Asp Ser Ser Lys Ser Gln Val Phe Leu
65                  70                  75                  80

Lys Met Ser Ser Leu Gln Ser Asp Asp Thr Ala Arg Tyr Tyr Cys Ala
                85                  90                  95

Gly Asp Gly Tyr Tyr Pro Tyr Ala Met Asp Asn Trp Gly His Gly Thr
            100                 105                 110

Ser Val Thr Val Ser Ser
        115

<210> SEQ ID NO 5
<211> LENGTH: 118
<212> TYPE: PRT
<213> ORGANISM: Murinae gen. sp.
<220> FEATURE:
<221> NAME/KEY: CHAIN
<222> LOCATION: (1)..(118)
<223> OTHER INFORMATION: VARIABLE REGION OF LIGHT CHAIN OF MONOCLONAL
      ANTIBODY 228A-4

<400> SEQUENCE: 5

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Asn Ile Asn Trp Ile Arg Gln Pro Pro Gly Lys Gly Leu Glu Trp Leu
        35                  40                  45

Gly Met Ile Trp Gly Asp Gly Ser Thr Ala Tyr Asn Ser Ala Leu Lys
    50                  55                  60

Ser Arg Leu Ser Ile Ser Lys Asp Asn Ser Lys Ser Gln Ile Phe Leu
65                  70                  75                  80

Lys Met Asn Ser Leu Gln Thr Glu Asp Thr Ala Arg Tyr Tyr Cys Ala
                85                  90                  95

Arg Asp Gly Tyr Phe Pro Tyr Ala Met Ala Tyr Trp Gly Gln Gly Thr
            100                 105                 110

Ser Val Thr Val Ser Ser
        115

<210> SEQ ID NO 6
<211> LENGTH: 118

```
<212> TYPE: PRT
<213> ORGANISM: Murinae gen. sp.
<220> FEATURE:
<221> NAME/KEY: CHAIN
<222> LOCATION: (1)..(118)
<223> OTHER INFORMATION: VARIABLE REGION OF HEAVY CHAIN OF MONOCLONAL
      ANTIBODY 228A-4

<400> SEQUENCE: 6

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Asn Ile Asn Trp Ile Arg Gln Pro Pro Gly Lys Gly Leu Glu Trp Leu
        35                  40                  45

Gly Met Ile Trp Gly Asp Gly Ser Thr Ala Tyr Asn Ser Ala Leu Lys
    50                  55                  60

Ser Arg Leu Ser Ile Ser Lys Asp Asn Ser Lys Ser Gln Ile Phe Leu
65                  70                  75                  80

Lys Met Asn Ser Leu Gln Thr Glu Asp Thr Ala Arg Tyr Tyr Cys Ala
                85                  90                  95

Arg Asp Gly Tyr Phe Pro Tyr Ala Met Ala Tyr Trp Gly Gln Gly Thr
            100                 105                 110

Ser Val Thr Val Ser Ser
            115

<210> SEQ ID NO 7
<211> LENGTH: 114
<212> TYPE: PRT
<213> ORGANISM: Murinae gen. sp.
<220> FEATURE:
<221> NAME/KEY: CHAIN
<222> LOCATION: (1)..(114)
<223> OTHER INFORMATION: VARIABLE REGION OF LIGHT CHAIN OF MONOCLONAL
      ANTIBODY 227-26
<220> FEATURE:
<221> NAME/KEY: CHAIN
<222> LOCATION: (1)..(114)
<223> OTHER INFORMATION: VARIABLE REGION OF LIGHT CHAIN OF MONOCLONAL
      ANTIBODY 227-26-1

<400> SEQUENCE: 7

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala

<210> SEQ ID NO 8
<211> LENGTH: 120
<212> TYPE: PRT
```

-continued

```
<213> ORGANISM: Murinae gen. sp.
<220> FEATURE:
<221> NAME/KEY: CHAIN
<222> LOCATION: (1)..(120)
<223> OTHER INFORMATION: VARIABLE REGION OF HEAVY CHAIN OF MONOCLONAL
      ANTIBODY 227-26-1

<400> SEQUENCE: 8

Gln Val Gln Leu Gln Gln Ser Gly Asp Asp Leu Val Leu Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Arg Pro Gly Gln Gly Leu Glu Trp Ile
        35                  40                  45

Gly His Ile Ala Pro Gly Ser Gly Ser Thr Tyr Phe Asn Glu Met Phe
    50                  55                  60

Lys Gly Lys Ala Thr Leu Thr Val Asp Thr Ser Ser Ser Thr Ala Tyr
65                  70                  75                  80

Ile Gln Leu Ser Ser Leu Ser Ser Glu Asp Ser Ala Val Tyr Phe Cys
                85                  90                  95

Ala Arg Ser Asp Ile Phe Leu Ser Tyr Ala Met Asp Tyr Trp Gly Gln
            100                 105                 110

Gly Thr Ser Val Thr Val Ser Ser
        115                 120

<210> SEQ ID NO 9
<211> LENGTH: 50
<212> TYPE: DNA
<213> ORGANISM: ARTIFICIAL
<220> FEATURE:
<223> OTHER INFORMATION: Forward oligonucleotide primer for a mutant
      IL13 sequence

<400> SEQUENCE: 9
aagctttccc caggccctgt gcctccctct acagccctca ggaagctcat            50

<210> SEQ ID NO 10
<211> LENGTH: 30
<212> TYPE: DNA
<213> ORGANISM: ARTIFICIAL
<220> FEATURE:
<223> OTHER INFORMATION: Reverse Oligo nucleotide primer of a mutant
      IL13 sequence

<400> SEQUENCE: 10
ctcgaggttg aaccgtccct cgcgaaaaag                                  30

<210> SEQ ID NO 11
<211> LENGTH: 22
<212> TYPE: DNA
<213> ORGANISM: ARTIFICIAL
<220> FEATURE:
<223> OTHER INFORMATION: Forward degenerate oligonucleotide primer for
      monkey IL13

<400> SEQUENCE: 11
gyyctrggcy ycatggcgct yt                                          22

<210> SEQ ID NO 12
<211> LENGTH: 25
<212> TYPE: DNA
<213> ORGANISM: ARTIFICIAL
<220> FEATURE:
<223> OTHER INFORMATION: Reverse degenerate oligonucleotide primer for
``` monkey IL13

<400> SEQUENCE: 12
tttcagttga accgtccyty gcgaa                                          25

<210> SEQ ID NO 13
<211> LENGTH: 399
<212> TYPE: DNA
<213> ORGANISM: Macaca fascicularis

<400> SEQUENCE: 13
atggcgctct tgttgaccat ggtcattgct ctcacttgcc tcggcggctt tgcctcccca    60
agccctgtgc ctccctctac agccctcaag gagctcattg aggagctggt caacatcacc   120
cagaaccaga aggccccgct ctgcaatggc agcatggtgt ggagcatcaa cctgacagct   180
ggcgtgtact gtgcagccct ggaatccctg atcaacgtgt caggctgcag tgccatcgag   240
aagacccaga ggatgctgaa cggattctgc ccgcacaagg tctcagctgg cagttttcc    300 agcttgcgtg tccgagacac caaaatcgag gtggcccagt ttgtaaagga cctgctcgta   360
catttaaaga aacttttcg caatggacgg ttcaactga                           399

<210> SEQ ID NO 14
<211> LENGTH: 34
<212> TYPE: DNA
<213> ORGANISM: ARTIFICIAL
<220> FEATURE:
<223> OTHER INFORMATION: Forward oligonucleotide primer for cynomologus
      monkey IL13

<400> SEQUENCE: 14
aagcttcacc atggcgctct tgttgaccat ggtc                                34

<210> SEQ ID NO 15
<211> LENGTH: 40
<212> TYPE: DNA
<213> ORGANISM: ARTIFICIAL
<220> FEATURE:
<223> OTHER INFORMATION: Reverse oligonucleotide primer for cynomologus
      monkey IL13

<400> SEQUENCE: 15
tcacaagatc tgggctcctc gaggttgaac cgtccattgc                          40

<210> SEQ ID NO 16
<211> LENGTH: 23
<212> TYPE: DNA
<213> ORGANISM: ARTIFICIAL
<220> FEATURE:
<223> OTHER INFORMATION: Forward oligonucleotide primer for Fc gamma1

<400> SEQUENCE: 16
ctcgaggagc ccagatcttg tga                                            23

<210> SEQ ID NO 17
<211> LENGTH: 35
<212> TYPE: DNA
<213> ORGANISM: ARTIFICIAL
<220> FEATURE:
<223> OTHER INFORMATION: Reverse oligonucleotide primer for Fc gamma 1

<400> SEQUENCE: 17
gctctagagc ctcatttacc cggagacagg gagag                               35

<210> SEQ ID NO 18
<211> LENGTH: 8
<212> TYPE: PRT
<213> ORGANISM: ARTIFICIAL
<220> FEATURE:
<223> OTHER INFORMATION: EPITOPE BINDING SITE

<400> SEQUENCE: 18

Glu Ser Leu Ile Asn Val Ser Gly
1               5

<210> SEQ ID NO 19
<211> LENGTH: 12
<212> TYPE: PRT
<213> ORGANISM: ARTIFICIAL
<220> FEATURE:
<223> OTHER INFORMATION: EPITOPE BINDING SITE

<400> SEQUENCE: 19

Tyr Cys Ala Ala Leu Glu Ser Leu Ile Asn Val Ser
1               5                   10

<210> SEQ ID NO 20
<211> LENGTH: 23
<212> TYPE: PRT
<213> ORGANISM: ARTIFICIAL
<220> FEATURE:
<223> OTHER INFORMATION: FRL1 228B/C-1

<400> SEQUENCE: 20

Asn Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 21
<211> LENGTH: 23
<212> TYPE: PRT
<213> ORGANISM: ARTIFICIAL
<220> FEATURE:
<223> OTHER INFORMATION: FRL1 TEMPLATE HT2

<400> SEQUENCE: 21

Asp Ile Val Met Thr Gln Ser Pro Asp Ser Leu Ser Val Ser Leu Gly
1               5                   10                  15

Glu Arg Ala Thr Ile Asn Cys
            20

<210> SEQ ID NO 22
<211> LENGTH: 23
<212> TYPE: PRT
<213> ORGANISM: ARTIFICIAL
<220> FEATURE:
<223> OTHER INFORMATION: FRL1 VARIANT B

<400> SEQUENCE: 22

Asp Ile Val Met Thr Gln Ser Pro Ala Ser Leu Ala Val Ser Leu Gly
1               5                   10                  15

Glu Arg Ala Thr Ile Asn Cys
            20

<210> SEQ ID NO 23
<211> LENGTH: 23
<212> TYPE: PRT
<213> ORGANISM: ARTIFICIAL
<220> FEATURE:

<223> OTHER INFORMATION: FRL1 VARIANT J

<400> SEQUENCE: 23

Asp Ile Val Leu Thr Gln Ser Pro Asp Ser Leu Ala Val Ser Leu Gly
1               5                   10                  15

Glu Arg Ala Thr Ile Asn Cys
            20

<210> SEQ ID NO 24
<211> LENGTH: 23
<212> TYPE: PRT
<213> ORGANISM: ARTIFICIAL
<220> FEATURE:
<223> OTHER INFORMATION: FRL1 VARIANT L

<400> SEQUENCE: 24

Asp Ile Val Leu Thr Gln Ser Pro Ala Ser Leu Ser Val Ser Leu Gly
1               5                   10                  15

Glu Arg Ala Thr Ile Asn Cys
            20

<210> SEQ ID NO 25
<211> LENGTH: 23
<212> TYPE: PRT
<213> ORGANISM: ARTIFICIAL
<220> FEATURE:
<223> OTHER INFORMATION: FRL1 VARIANT HT-NEW #300

<400> SEQUENCE: 25

Asp Ile Val Leu Thr Gln Ser Pro Asp Ser Leu Ser Val Ser Leu Gly
1               5                   10                  15

Glu Arg Ala Thr Ile Asn Cys
            20

<210> SEQ ID NO 26
<211> LENGTH: 23
<212> TYPE: PRT
<213> ORGANISM: ARTIFICIAL
<220> FEATURE:
<223> OTHER INFORMATION: FRL1 VARIANT HT2-DP27 #29

<400> SEQUENCE: 26

Asp Ile Val Leu Thr Gln Ser Pro Val Ser Leu Ala Val Ser Leu Gly
1               5                   10                  15

Glu Arg Ala Thr Ile Asn Cys
            20

<210> SEQ ID NO 27
<211> LENGTH: 23
<212> TYPE: PRT
<213> ORGANISM: ARTIFICIAL
<220> FEATURE:
<223> OTHER INFORMATION: FRL1 VARIANT HT2-DP27 #53

<400> SEQUENCE: 27

Asp Ile Val Met Thr Gln Ser Pro Ala Ser Leu Ser Val Ser Leu Gly
1               5                   10                  15

Glu Arg Ala Thr Ile Asn Cys
            20

<210> SEQ ID NO 28
<211> LENGTH: 23
<212> TYPE: PRT
<213> ORGANISM: ARTIFICIAL

```
<220> FEATURE:
<223> OTHER INFORMATION: FRL1 VARIANT HT2-DP27 #66

<400> SEQUENCE: 28

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 29
<211> LENGTH: 15
<212> TYPE: PRT
<213> ORGANISM: ARTIFICIAL
<220> FEATURE:
<223> OTHER INFORMATION: FRL2 228B/C

<400> SEQUENCE: 29

Trp Tyr Gln Gln Lys Pro Gly Gln Pro Pro Lys Leu Leu Ile Tyr
1               5                   10                  15

<210> SEQ ID NO 30
<211> LENGTH: 32
<212> TYPE: PRT
<213> ORGANISM: ARTIFICIAL
<220> FEATURE:
<223> OTHER INFORMATION: FRL3 288 B/C

<400> SEQUENCE: 30

Gly Val Pro Ala Arg Phe Ser Gly Ser Gly Ser Arg Thr Asp Phe Thr
1               5                   10                  15

Leu Thr Ile Asp Pro Val Glu Ala Asp Asp Ala Ala Ser Tyr Tyr Cys
            20                  25                  30

<210> SEQ ID NO 31
<211> LENGTH: 32
<212> TYPE: PRT
<213> ORGANISM: ARTIFICIAL
<220> FEATURE:
<223> OTHER INFORMATION: FRL3 HT2

<400> SEQUENCE: 31

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 32
<211> LENGTH: 32
<212> TYPE: PRT
<213> ORGANISM: ARTIFICIAL
<220> FEATURE:
<223> OTHER INFORMATION: FRL3 VARIANT B

<400> SEQUENCE: 32

Gly Val Pro Asp Arg Phe Ser Gly Ser Gly Ser Gly Thr Asp Phe Thr
1               5                   10                  15

Leu Thr Ile Asp Pro Leu Gln Ala Glu Asp Val Ala Val Tyr Tyr Cys
            20                  25                  30

<210> SEQ ID NO 33
<211> LENGTH: 32
<212> TYPE: PRT
<213> ORGANISM: ARTIFICIAL
<220> FEATURE:
<223> OTHER INFORMATION: FRL3 VARIANT J
```

-continued

```
<400> SEQUENCE: 33

Gly Val Pro Asp Arg Phe Ser Gly Ser Gly Ser Gly Thr Asp Phe Thr
1               5                   10                  15

Leu Thr Ile Asp Ser Leu Gln Ala Glu Asp Val Ala Val Tyr Tyr Cys
            20                  25                  30

<210> SEQ ID NO 34
<211> LENGTH: 32
<212> TYPE: PRT
<213> ORGANISM: ARTIFICIAL
<220> FEATURE:
<223> OTHER INFORMATION: FRL3 VARIANT L

<400> SEQUENCE: 34

Gly Val Pro Asp Arg Phe Ser Gly Ser Gly Ser Arg Thr Asp Phe Thr
1               5                   10                  15

Leu Thr Ile Asp Pro Leu Gln Ala Glu Asp Val Ala Val Tyr Tyr Cys
            20                  25                  30

<210> SEQ ID NO 35
<211> LENGTH: 32
<212> TYPE: PRT
<213> ORGANISM: ARTIFICIAL
<220> FEATURE:
<223> OTHER INFORMATION: FRL3 VARIANT N

<400> SEQUENCE: 35

Gly Val Pro Asp Arg Phe Ser Gly Ser Gly Ser Arg Thr Asp Phe Thr
1               5                   10                  15

Leu Thr Ile Asp Pro Val Gln Ala Glu Asp Val Ala Val Tyr Tyr Cys
            20                  25                  30

<210> SEQ ID NO 36
<211> LENGTH: 32
<212> TYPE: PRT
<213> ORGANISM: ARTIFICIAL
<220> FEATURE:
<223> OTHER INFORMATION: FRL3 VARIANT P

<400> SEQUENCE: 36

Gly Val Pro Asp Arg Phe Ser Gly Ser Gly Ser Arg Thr Asp Phe Thr
1               5                   10                  15

Leu Thr Ile Asp Ser Val Gln Ala Glu Asp Val Ala Val Tyr Tyr Cys
            20                  25                  30

<210> SEQ ID NO 37
<211> LENGTH: 32
<212> TYPE: PRT
<213> ORGANISM: ARTIFICIAL
<220> FEATURE:
<223> OTHER INFORMATION: FRL3 VARIANT R

<400> SEQUENCE: 37

Gly Val Pro Asp Arg Phe Ser Gly Ser Gly Ser Arg Thr Asp Phe Thr
1               5                   10                  15

Leu Thr Ile Ser Ser Val Gln Ala Glu Asp Val Ala Val Tyr Tyr Cys
            20                  25                  30

<210> SEQ ID NO 38
<211> LENGTH: 32
<212> TYPE: PRT
<213> ORGANISM: ARTIFICIAL
<220> FEATURE:
```

```
<223> OTHER INFORMATION: FRL3 VARIANT HT2-NEW #1

<400> SEQUENCE: 38

Gly Val Pro Asp Arg Phe Ser Gly Ser Gly Ser Arg Thr Asp Phe Thr
1               5                   10                  15

Leu Thr Ile Ser Pro Val Gln Ala Glu Asp Val Ala Val Tyr Tyr Cys
            20                  25                  30

<210> SEQ ID NO 39
<211> LENGTH: 32
<212> TYPE: PRT
<213> ORGANISM: ARTIFICIAL
<220> FEATURE:
<223> OTHER INFORMATION: FRL3 VARIANT HT2-NEW #9

<400> SEQUENCE: 39

Gly Val Pro Asp Arg Phe Ser Gly Ser Gly Ser Gly Thr Asp Phe Thr
1               5                   10                  15

Leu Thr Ile Ser Ser Val Glu Ala Glu Asp Val Ala Val Tyr

```
<220> FEATURE:
<223> OTHER INFORMATION: FRL3 VARIANT HT2-NEW #74

<400> SEQUENCE: 43

Gly Val Pro Asp Arg Phe Ser Gly Ser Gly Ser Gly Thr Asp Phe Thr
1               5                   10                  15

Leu Thr Ile Ser Pro Val Gln Ala Glu Asp Val Ala Val Tyr Tyr Cys
            20                  25                  30

<210> SEQ ID NO 44
<211> LENGTH: 32
<212> TYPE: PRT
<213> ORGANISM: ARTIFICIAL
<220> FEATURE:
<223> OTHER INFORMATION: FRL3 VARIANT HT2-NEW #78

<400> SEQUENCE: 44

Gly Val Pro Asp Arg Phe Ser Gly Ser Gly Ser Gly Thr Asp Phe Thr
1               5                   10                  15

Leu Thr Ile Asp Ser Val Glu Ala Glu Asp Val Ala Val Tyr Tyr Cys
            20                  25                  30

<210> SEQ ID NO 45
<211> LENGTH: 32
<212> TYPE: PRT
<213> ORGANISM: ARTIFICIAL
<220> FEATURE:
<223> OTHER INFORMATION: FRL3 VARIANT HT2-NEW #322

<400> SEQUENCE: 45

Gly Val Pro Asp Arg Phe Ser Gly Ser Gly Ser Arg Thr Asp Phe Thr
1               5                   10                  15

Leu Thr Ile Asp Ser Leu Glu Ala Glu Asp Val Ala Val Tyr Tyr Cys
            20                  25                  30

<210> SEQ ID NO 46
<211> LENGTH: 32
<212> TYPE: PRT
<213> ORGANISM: ARTIFICIAL
<220> FEATURE:
<223> OTHER INFORMATION: FRL3 VARIANT HT2-NEW #162

<400> SEQUENCE: 46

Gly Val Pro Asp Arg Phe Ser Gly Ser Gly Ser Gly Thr Asp Phe Thr
1               5                   10                  15

Leu Thr Ile Asp Pro Val Gln Ala Glu Asp Val Ala Val Tyr Tyr Cys
            20                  25                  30

<210> SEQ ID NO 47
<211> LENGTH: 32
<212> TYPE: PRT
<213> ORGANISM: ARTIFICIAL
<220> FEATURE:
<223> OTHER INFORMATION: FRL3 VARIANT HT2-DP27 # 7

<400> SEQUENCE: 47

Gly Val Pro Asp Arg Phe Ser Gly Ser Gly Ser Gly Thr Asp Phe Thr
1               5                   10                  15

Leu Thr Ile Asp Ser Val Gln Ala Glu Asp Val Ala Val Tyr Tyr Cys
            20                  25                  30

<210> SEQ ID NO 48
<211> LENGTH: 32
<212> TYPE: PRT
```

<213> ORGANISM: ARTIFICIAL
<220> FEATURE:
<223> OTHER INFORMATION: FRL3 VARIANT HT2-DP27 #57

<400> SEQUENCE: 48

Gly Val Pro Asp Arg Phe Ser Gly Ser Gly Ser Gly Thr Asp Phe Thr
1               5                   10                  15

Leu Thr Ile Ser Pro Val Glu Ala Glu Asp Val Ala Val Tyr Tyr Cys
            20                  25                  30

<210> SEQ ID NO 49
<211> LENGTH: 32
<212> TYPE: PRT
<213> ORGANISM: ARTIFICIAL
<220> FEATURE:
<223> OTHER INFORMATION: FRL3 VARIANT HT2-DP27 #73

<400> SEQUENCE: 49

Gly Val Pro Asp Arg Phe Ser Gly Ser Gly Ser Gly Thr Asp Phe Thr
1               5                   10                  15

Leu Thr Ile Asp Pro Val Glu Ala Glu Asp Val Ala Val Tyr Tyr Cys
            20                  25                  30

<210> SEQ ID NO 50
<211> LENGTH: 32
<212> TYPE: PRT
<213> ORGANISM: ARTIFICIAL
<220> FEATURE:
<223> OTHER INFORMATION: FRL3 VARIANT HT2-DP27 #92

<400> SEQUENCE: 50

Gly Val Pro Asp Arg Phe Ser Gly Ser Gly Ser Gly Thr Asp Phe Thr
1               5                   10                  15

Leu Thr Ile Asp Thr Val Gln Ala Glu Asp Val Ala Val Tyr Tyr Cys
            20                  25                  30

<210> SEQ ID NO 51
<211> LENGTH: 32
<212> TYPE: PRT
<213> ORGANISM: ARTIFICIAL
<220> FEATURE:
<223> OTHER INFORMATION: FRL3 VARIANT HT2-DP27 #118

<400> SEQUENCE: 51

Gly Val Pro Asp Arg Phe Ser Gly Ser Gly Ser Arg Thr Asp Phe Thr
1               5                   10                  15

Leu Thr Ile Ser Pro Leu Gln Ala Glu Asp Val Ala Val Tyr Tyr Cys
            20                  25                  30

<210> SEQ ID NO 52
<211> LENGTH: 32
<212> TYPE: PRT
<213> ORGANISM: ARTIFICIAL
<220> FEATURE:
<223> OTHER INFORMATION: FRL3 VARIANT HT2-DP27 #123

<400> SEQUENCE: 52

Gly Val Pro Asp Arg Phe Ser Gly Ser Gly Ser Arg Thr Asp Phe Thr
1               5                   10                  15

Leu Thr Ile Ser Ser Leu Glu Ala Glu Asp Val Ala Val Tyr Tyr Cys
            20                  25                  30

<210> SEQ ID NO 53
<211> LENGTH: 32

```
<212> TYPE: PRT
<213> ORGANISM: ARTIFICIAL
<220> FEATURE:
<223> OTHER INFORMATION: FRL3 VARIANT HT2-DP27 #83

<400> SEQUENCE: 53

Gly Val Pro Asp Arg Phe Ser Gly Ser Gly Ser Arg Thr Asp Phe Thr
1               5                   10                  15
Leu Thr Ile Asp Pro Leu Glu Ala Glu Asp Val Ala Val Tyr Tyr Cys
            20                  25                  30

<210> SEQ ID NO 54
<211> LENGTH: 32
<212> TYPE: PRT
<213> ORGANISM: ARTIFICIAL
<220> FEATURE:
<223> OTHER INFORMATION: FRL3 VARIANT HT2-DP27 #135

<400> SEQUENCE: 54

Gly Val Pro Asp Arg Phe Ser Gly Ser Gly Ser Gly Thr Asp Phe Thr
1               5                   10                  15
Leu Thr Ile Ser Ser Leu Glu Ala Glu Asp Val Ala Val Tyr Tyr Cys
            20                  25                  30

<210> SEQ ID NO 55
<211> LENGTH: 32
<212> TYPE: PRT
<213> ORGANISM: ARTIFICIAL
<220> FEATURE:
<223> OTHER INFORMATION: FRL3 VARIANT HT2-DP27 #273

<400> SEQUENCE: 55

Gly Val Pro Asp Arg Phe Ser Gly Ser Gly Ser Gly Thr Asp Phe Thr
1               5                   10                  15
Leu Thr Ile Ser Ser Val Gln Ala Glu Asp Val Ala Val Tyr Tyr Cys
            20                  25                  30

<210> SEQ ID NO 56
<211> LENGTH: 32
<212> TYPE: PRT
<213> ORGANISM: ARTIFICIAL
<220> FEATURE:
<223> OTHER INFORMATION: FRL3 VARIANT HT2-DP27 #301

<400> SEQUENCE: 56

Gly Val Pro Asp Arg Phe Ser Gly Ser Gly Ser Gly Thr Asp Phe Thr
1               5                   10                  15
Leu Thr Ile Ser Pro Leu Gln Ala Glu Asp Val Ala Val Tyr Tyr Cys
            20                  25                  30

<210> SEQ ID NO 57
<211> LENGTH: 12
<212> TYPE: PRT
<213> ORGANISM: ARTIFICIAL
<220> FEATURE:
<223> OTHER INFORMATION: FRL4 228 B/C

<400> SEQUENCE: 57

Phe Gly Gly Gly Thr Lys Leu Glu Ile Lys Arg Ala
1               5                   10

<210> SEQ ID NO 58
<211> LENGTH: 11
<212> TYPE: PRT
<213> ORGANISM: ARTIFICIAL
```

```
<220> FEATURE:
<223> OTHER INFORMATION: FRL4 HT2

<400> SEQUENCE: 58

Phe Gly Gly Gly Thr Lys Val Glu Ile Lys Arg
1               5                   10

<210> SEQ ID NO 59
<211> LENGTH: 11
<212> TYPE: PRT
<213> ORGANISM: ARTIFICIAL
<220> FEATURE:
<223> OTHER INFORMATION: FRL4 VARIANT B

<400> SEQUENCE: 59

Phe Gly Gly Gly Thr Lys Leu Glu Ile Lys Arg
1               5                   10

<210> SEQ ID NO 60
<211> LENGTH: 30
<212> TYPE: PRT
<213> ORGANISM: ARTIFICIAL
<220> FEATURE:
<223> OTHER INFORMATION: FRH1 228 B/C

<400> SEQUENCE: 60

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Asn
            20                  25                  30

<210> SEQ ID NO 61
<211> LENGTH: 30
<212> TYPE: PRT
<213> ORGANISM: ARTIFICIAL
<220> FEATURE:
<223> OTHER INFORMATION: FRH1 DP27

<400> SEQUENCE: 61

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 62
<211> LENGTH: 30
<212> TYPE: PRT
<213> ORGANISM: ARTIFICIAL
<220> FEATURE:
<223> OTHER INFORMATION: FRH1 NEW

<400> SEQUENCE: 62

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser
            20                  25                  30

<210> SEQ ID NO 63
<211> LENGTH: 30
<212> TYPE: PRT
<213> ORGANISM: ARTIFICIAL
<220> FEATURE:
<223> OTHER INFORMATION: FRH1 VARIANT HT2-NEW #73

<400> SEQUENCE: 63
```

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser
            20                  25                  30
```

<210> SEQ ID NO 64
<211> LENGTH: 30
<212> TYPE: PRT
<213> ORGANISM: ARTIFICIAL
<220> FEATURE:
<223> OTHER INFORMATION: FRH1 HT2-DP27 #7

<400> SEQUENCE: 64

```
Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Asn
            20                  25                  30
```

<210> SEQ ID NO 65
<211> LENGTH: 30
<212> TYPE: PRT
<213> ORGANISM: ARTIFICIAL
<220> FEATURE:
<223> OTHER INFORMATION: FRH1 VARIANT HT2-DP27 #40

<400> SEQUENCE: 65

```
Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser
            20                  25                  30
```

<210> SEQ ID NO 66
<211> LENGTH: 30
<212> TYPE: PRT
<213> ORGANISM: ARTIFICIAL
<220> FEATURE:
<223> OTHER INFORMATION: FRH1 VARIANT HT2-DP27 #268

<400> SEQUENCE: 66

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Asn
            20                  25                  30
```

<210> SEQ ID NO 67
<211> LENGTH: 14
<212> TYPE: PRT
<213> ORGANISM: ARTIFICIAL
<220> FEATURE:
<223> OTHER INFORMATION: FRH2 228 B/C

<400> SEQUENCE: 67

```
Trp Val Arg Gln Pro Pro Gly Lys Gly Leu Glu Trp Leu Gly
1               5                   10
```

<210> SEQ ID NO 68
<211> LENGTH: 14
<212> TYPE: PRT
<213> ORGANISM: ARTIFICIAL
<220> FEATURE:
<223> OTHER INFORMATION: FRH2 DP27

<400> SEQUENCE: 68

```
Trp Ile Arg Gln Pro Pro Gly Lys Ala Leu Glu Trp Leu Ala
1               5                   10
```

```
<210> SEQ ID NO 69
<211> LENGTH: 14
<212> TYPE: PRT
<213> ORGANISM: ARTIFICIAL
<220> FEATURE:
<223> OTHER INFORMATION: FRH2 NEW

<400> SEQUENCE: 69

Trp Val Arg Gln Pro Pro Gly Arg Gly Leu Glu Trp Ile Gly
1               5                   10

<210> SEQ ID NO 70
<211> LENGTH: 14
<212> TYPE: PRT
<213> ORGANISM: ARTIFICIAL
<220> FEATURE:
<223> OTHER INFORMATION: FRH2 VARIANT 1

<400> SEQUENCE: 70

Trp Val Arg Gln Pro Pro Gly Lys Ala Leu Glu Trp Leu Gly
1               5                   10

<210> SEQ ID NO 71
<211> LENGTH: 14
<212> TYPE: PRT
<213> ORGANISM: ARTIFICIAL
<220> FEATURE:
<223> OTHER INFORMATION: FRH2 VARIANT 3

<400> SEQUENCE: 71

Trp Ile Arg Gln Pro Pro Gly Lys Gly Leu Glu Trp Leu Gly
1               5                   10

<210> SEQ ID NO 72
<211> LENGTH: 14
<212> TYPE: PRT
<213> ORGANISM: ARTIFICIAL
<220> FEATURE:
<223> OTHER INFORMATION: FRH2 VARIANT HT2-DP27 #7

<400> SEQUENCE: 72

Trp Ile Arg Gln Pro Pro Gly Lys Ala Leu Glu Trp Leu Gly
1               5                   10

<210> SEQ ID NO 73
<211> LENGTH: 14
<212> TYPE: PRT
<213> ORGANISM: ARTIFICIAL
<220> FEATURE:
<223> OTHER INFORMATION: FRH2 VARIANT HT2-DP27 # 43

<400> SEQUENCE: 73

Trp Ile Arg Gln Pro Pro Gly Lys Gly Leu Glu Trp Leu Ala
1               5                   10

<210> SEQ ID NO 74
<211> LENGTH: 14
<212> TYPE: PRT
<213> ORGANISM: ARTIFICIAL
<220> FEATURE:
<223> OTHER INFORMATION: FRH2 VARIANT HT2-DP27 #50

<400> SEQUENCE: 74

Trp Val Arg Gln Pro Pro Gly Lys Gly Leu Glu Trp Leu Ala
1               5                   10
```

```
<210> SEQ ID NO 75
<211> LENGTH: 14
<212> TYPE: PRT
<213> ORGANISM: ARTIFICIAL
<220> FEATURE:
<223> OTHER INFORMATION: FRH2 VARIANT HT2-DP27 #100

<400> SEQUENCE: 75

Trp Val Arg Gln Pro Pro Gly Lys Ala Leu Glu Trp Leu Ala
1               5                   10

<210> SEQ ID NO 76
<211> LENGTH: 32
<212> TYPE: PRT
<213> ORGANISM: ARTIFICIAL
<220> FEATURE:
<223> OTHER INFORMATION: FRH3 228 B/C

<400> SEQUENCE: 76

Arg Leu Asn Ile Ser Lys Asp Ser Ser Lys Ser Gln Val Phe Leu Lys
1               5                   10                  15

Met Ser Ser Leu Gln Ser Asp Asp Thr Ala Arg Tyr Tyr Cys Ala Gly
                20                  25                  30

<210> SEQ ID NO 77
<211> LENGTH: 32
<212> TYPE: PRT
<213> ORGANISM: ARTIFICIAL
<220> FEATURE:
<223> OTHER INFORMATION: FRH3 DP27

<400> SEQUENCE: 77

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
                20                  25                  30

<210> SEQ ID NO 78
<211> LENGTH: 32
<212> TYPE: PRT
<213> ORGANISM: ARTIFICIAL
<220> FEATURE:
<223> OTHER INFORMATION: FRH3 NEW

<400> SEQUENCE: 78

Arg Val Thr Met Leu Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
                20                  25                  30

<210> SEQ ID NO 79
<211> LENGTH: 32
<212> TYPE: PRT
<213> ORGANISM: ARTIFICIAL
<220> FEATURE:
<223> OTHER INFORMATION: FRH3 VARIANT 1

<400> SEQUENCE: 79

Arg Leu Thr Ile Ser Lys Asp Ser Ser Lys Asn Gln Val Val Leu Thr
1               5                   10                  15

Met Thr Asn Met Asp Pro Val Asp Thr Ala Thr Tyr Tyr Cys Ala Gly
                20                  25                  30

<210> SEQ ID NO 80
```

```
<211> LENGTH: 32
<212> TYPE: PRT
<213> ORGANISM: ARTIFICIAL
<220> FEATURE:
<223> OTHER INFORMATION: FRH3 VARIANT 3

<400> SEQUENCE: 80

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Gly
            20                  25                  30

<210> SEQ ID NO 81
<211> LENGTH: 32
<212> TYPE: PRT
<213> ORGANISM: ARTIFICIAL
<220> FEATURE:
<223> OTHER INFORMATION: FRH3 VARIANT 4

<400> SEQUENCE: 81

Arg Leu Thr Ile Ser Lys Asp Thr Ser Lys Asn Gln Val Val Leu Thr
1               5                   10                  15

Met Thr Asn Met Asp Pro Val Asp Thr Ala Arg Tyr Tyr Cys Ala Gly
            20                  25                  30

<210> SEQ ID NO 82
<211> LENGTH: 32
<212> TYPE: PRT
<213> ORGANISM: ARTIFICIAL
<220> FEATURE:
<223> OTHER INFORMATION: FRH3 HT2-NEW #1

<400> SEQUENCE: 82

Arg Leu Asn Met Ser Lys Asp Thr Ser Lys Asn Gln Phe Phe Leu Arg
1               5                   10                  15

Leu Ser Ser Val Thr Ala Ala Asp Thr Ala Val Tyr Tyr Cys Ala Gly
            20                  25                  30

<210> SEQ ID NO 83
<211> LENGTH: 32
<212> TYPE: PRT
<213> ORGANISM: ARTIFICIAL
<220> FEATURE:
<223> OTHER INFORMATION: FRH3 VARIANT HT2-NEW #9

<400> SEQUENCE: 83

Arg Leu Asn Met Ser Lys Asp Thr Ser Lys Asn Gln Phe Phe Leu Arg
1               5                   10                  15

Leu Ser Ser Val Thr Ala Ala Asp Thr Ala Arg Tyr Tyr Cys Ala Gly
            20                  25                  30

<210> SEQ ID NO 84
<211> LENGTH: 32
<212> TYPE: PRT
<213> ORGANISM: ARTIFICIAL
<220> FEATURE:
<223> OTHER INFORMATION: FRH3 VARIANT HT2-NEW #14

<400> SEQUENCE: 84

Arg Val Asn Met Ser Lys Asp Thr Ser Lys Asn Gln Phe Ser Leu Arg
1               5                   10                  15

Leu Ser Ser Val Thr Ala Ala Asp Thr Ala Val Tyr Tyr Cys Ala Arg
            20                  25                  30
```

<210> SEQ ID NO 85
<211> LENGTH: 32
<212> TYPE: PRT
<213> ORGANISM: ARTIFICIAL
<220> FEATURE:
<223> OTHER INFORMATION: FRH3 VARIANT HT2-DP27 #26

<400> SEQUENCE: 85

Arg Leu Asn Ile Ser Lys Asp Thr Ser Lys Asn Gln Val Val Leu Thr
1               5                   10                  15

Met Thr Asn Met Asp Pro Val Asp Thr Ala Arg Tyr Tyr Cys Ala Arg
            20                  25                  30

<210> SEQ ID NO 86
<211> LENGTH: 32
<212> TYPE: PRT
<213> ORGANISM: ARTIFICIAL
<220> FEATURE:
<223> OTHER INFORMATION: FRH3 VARIANT HT2-DP27 #275

<400> SEQUENCE: 86

Arg Leu Thr Ile Ser Lys Asp Ile Ser Lys Asn Gln Val Val Leu Thr
1 5 10 15

Met Thr Asn Met Asp Pro Val Asp Thr Ala Arg Tyr Tyr Cys Ala Gly
20 25 30

<210> SEQ ID NO 87
<211> LENGTH: 32
<212> TYPE: PRT
<213> ORGANISM: ARTIFICIAL
<220> FEATURE:
<223> OTHER INFORMATION: FRH3 VARIANT HT2-DP27 #301

<400> SEQUENCE: 87

Arg Leu Asn Ile Ser Lys Asp Thr Ser Lys Asn Gln Val Val Leu Thr
1 5 10 15

Met Thr Asn Met Asp Pro Val Asp Thr Ala Thr Tyr Tyr Cys Ala Gly
20 25 30

<210> SEQ ID NO 88
<211> LENGTH: 32
<212> TYPE: PRT
<213> ORGANISM: ARTIFICIAL
<220> FEATURE:
<223> OTHER INFORMATION: FRH3 VARIANT HT2-DP27 #580

<400> SEQUENCE: 88

Arg Leu Asn Ile Ser Lys Asp Ser Ser Lys Asn Gln Val Val Leu Thr
1 5 10 15

Met Thr Asn Met Asp Pro Val Asp Thr Ala Thr Tyr Tyr Cys Ala Gly
20 25 30

<210> SEQ ID NO 89
<211> LENGTH: 32
<212> TYPE: PRT
<213> ORGANISM: ARTIFICIAL
<220> FEATURE:
<223> OTHER INFORMATION: FRH3 VARIANT HT2-DP27 #345

<400> SEQUENCE: 89

Arg Leu Asn Ile Ser Lys Asp Thr Ser Lys Asn Gln Val Val Leu Thr
1 5 10 15

Met Thr Asn Met Asp Pro Val Asp Thr Ala Thr Tyr Tyr Cys Ala Arg
20 25 30

-continued

```
<210> SEQ ID NO 90
<211> LENGTH: 32
<212> TYPE: PRT
<213> ORGANISM: ARTIFICIAL
<220> FEATURE:
<223> OTHER INFORMATION: FRH3 VARIANT HT2-DP27 #634

<400> SEQUENCE: 90

Arg Leu Thr Ile Ser Lys Asp Ser Ser Lys Asn Gln Val Val Leu Thr
1               5                   10                  15

Met Thr Asn Met Asp Pro Val Asp Thr Ala Arg Tyr Tyr Cys Ala Gly
            20                  25                  30

<210> SEQ ID NO 91
<211> LENGTH: 11
<212> TYPE: PRT
<213> ORGANISM: ARTIFICIAL
<220> FEATURE:
<223> OTHER INFORMATION: FRH4 228B/C

<400> SEQUENCE: 91

Trp Gly His Gly Thr Ser Val Thr Val Ser Ser
1               5                   10

<210> SEQ ID NO 92
<211> LENGTH: 11
<212> TYPE: PRT
<213> ORGANISM: ARTIFICIAL
<220> FEATURE:
<223> OTHER INFORMATION: FRH4 DP27

<400> SEQUENCE: 92

Trp Gly Gln Gly Ser Leu Val Thr Val Ser Ser
1               5                   10

<210> SEQ ID NO 93
<211> LENGTH: 112
<212> TYPE: PRT
<213> ORGANISM: ARTIFICIAL
<220> FEATURE:
<223> OTHER INFORMATION: VARIABLE LIGHT CHAIN OF CL5

<400> SEQUENCE: 93

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Gln Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Ala
                85                  90                  95

Glu Asp Pro Arg Thr Phe Gly Gly Gly Thr Lys Val Glu Ile Lys Arg
            100                 105                 110

<210> SEQ ID NO 94
<211> LENGTH: 118
<212> TYPE: PRT
<213> ORGANISM: ARTIFICIAL
<220> FEATURE:
```

<223> OTHER INFORMATION: VARIABLE HEAVY CHAIN OF CL5

<400> SEQUENCE: 94

```
Gln Val Thr Leu Arg Glu Ser Gly Pro Ala Leu Val Lys Pro Thr Gln
1               5                   10                  15

Thr Leu Thr Leu Thr Cys Thr Gly Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Lys Asn Trp Gly Gln Gly Ser
            100                 105                 110

Leu Val Thr Val Ser Ser
        115
```

<210> SEQ ID NO 95
<211> LENGTH: 112
<212> TYPE: PRT
<213> ORGANISM: ARTIFICIAL
<220> FEATURE:
<223> OTHER INFORMATION: VARIABLE LIGHT CHAIN OF CL-13

<400> SEQUENCE: 95

```
Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Gln Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110
```

<210> SEQ ID NO 96
<211> LENGTH: 118
<212> TYPE: PRT
<213> ORGANISM: ARTIFICIAL
<220> FEATURE:
<223> OTHER INFORMATION: VARIABLE HEAVY CHAIN OF CL-13

<400> SEQUENCE: 96

```
Gln Val Thr Leu Arg Glu Ser Gly Pro Ala Leu Val Lys Pro Thr Gln
1               5                   10                  15

Thr Leu Thr Leu Thr Cys Thr Gly Ser Gly Phe Ser Leu Ser Ala Lys
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
```

```
                  50                  55                  60
Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Val Asp Gly Tyr Tyr Pro Tyr Ala Met Ser Asn Trp Gly Gln Gly Ser
                100                 105                 110

Leu Val Thr Val Ser Ser
            115

<210> SEQ ID NO 97
<211> LENGTH: 112
<212> TYPE: PRT
<213> ORGANISM: ARTIFICIAL
<220> FEATURE:
<223> OTHER INFORMATION: VARIABLE LIGHT CHAIN OF CL-50

<400> SEQUENCE: 97

Asp Ile Val Met Thr Gln Ser Pro Asp Ser Leu Ser Val Ser Leu Gly
 1               5                  10                  15

Glu Arg Ala Thr Ile Asn Cys Arg Ala Ser Lys Ser Val Asp Ser Tyr
                 20                  25                  30

Gly Gln Ser Phe Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Ala
                 85                  90                  95

Glu Asp Pro Arg Thr Phe Gly Gly Gly Thr Lys Val Glu Ile Lys Arg
                100                 105                 110

<210> SEQ ID NO 98
<211> LENGTH: 118
<212> TYPE: PRT
<213> ORGANISM: ARTIFICIAL
<220> FEATURE:
<223> OTHER INFORMATION: VARIABLE HEAVY CHAIN OF CL-50

<400> SEQUENCE: 98

Gln Val Thr Leu Arg Glu Ser Gly Pro Ala Leu Val Lys Pro Thr Gln
 1               5                  10                  15

Thr Leu Thr Leu Thr Cys Thr Gly Ser Gly Phe Ser Leu Ser Ala Lys
                 20                  25                  30

Ser Val Asn Trp Ile Arg Gln Pro Pro Gly Lys Ala Leu Glu Trp Leu
             35                  40                  45

Ala Met Ile Trp Gly Asp Gly Lys Ile Val Tyr Asn Ser Ala Leu Lys
 50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Val Asp Gly Tyr Tyr Pro Tyr Ala Met Lys Asn Trp Gly Gln Gly Ser
                100                 105                 110

Leu Val Thr Val Ser Ser
            115
```

```
<210> SEQ ID NO 99
<211> LENGTH: 15
<212> TYPE: PRT
<213> ORGANISM: ARTIFICIAL
<220> FEATURE:
<223> OTHER INFORMATION: CDR-L1 228B/C

<400> SEQUENCE: 99

Arg Ala Ser Lys Ser Val Asp Ser Tyr Gly Asn Ser Phe Met His
1               5                   10                  15

<210> SEQ ID NO 100
<211> LENGTH: 15
<212> TYPE: PRT
<213> ORGANISM: ARTIFICIAL
<220> FEATURE:
<223> OTHER INFORMATION: CDR-L1 VARIANT 1

<400> SEQUENCE: 100

Arg Ala Ser Lys Ser Val Asp Ser Tyr Gly Gln Ser Phe Met His
1               5                   10                  15

<210> SEQ ID NO 101
<211> LENGTH: 15
<212> TYPE: PRT
<213> ORGANISM: ARTIFICIAL
<220> FEATURE:
<223> OTHER INFORMATION: CDR-L1 VARIANT 2

<400> SEQUENCE: 101

Arg Ala Ser Lys Ser Val Asp Ser Tyr Gly Gln Ser Phe Leu His
1               5                   10                  15

<210> SEQ ID NO 102
<211> LENGTH: 15
<212> TYPE: PRT
<213> ORGANISM: ARTIFICIAL
<220> FEATURE:
<223> OTHER INFORMATION: CDR-L1 VARIANT 3

<400> SEQUENCE: 102

Arg Ala Ser Lys Ser Val Asp Ser Tyr Gly Asn Ser Tyr Met His
1               5                   10                  15

<210> SEQ ID NO 103
<211> LENGTH: 15
<212> TYPE: PRT
<213> ORGANISM: ARTIFICIAL
<220> FEATURE:
<223> OTHER INFORMATION: CDR-L1 VARIANT 4

<400> SEQUENCE: 103

Arg Ala Ser Lys Ser Val Asp Ser Tyr Gly Asn Ser Phe Leu His
1               5                   10                  15

<210> SEQ ID NO 104
<211> LENGTH: 7
<212> TYPE: PRT
<213> ORGANISM: ARTIFICIAL
<220> FEATURE:
<223> OTHER INFORMATION: CDR-L2 228B/C

<400> SEQUENCE: 104

Leu Ala Ser Asn Leu Glu Ser
1               5
```

```
<210> SEQ ID NO 105
<211> LENGTH: 7
<212> TYPE: PRT
<213> ORGANISM: ARTIFICIAL
<220> FEATURE:
<223> OTHER INFORMATION: CDR-L2 VARIANT 1

<400> SEQUENCE: 105

Leu Ala Ser Asn Leu Asn Ser
1               5

<210> SEQ ID NO 106
<211> LENGTH: 7
<212> TYPE: PRT
<213> ORGANISM: ARTIFICIAL
<220> FEATURE:
<223> OTHER INFORMATION: CDR-L2 VARIANT 2

<400> SEQUENCE: 106

Leu Ala Ser Asn Leu Gln Ser
1               5

<210> SEQ ID NO 107
<211> LENGTH: 7
<212> TYPE: PRT
<213> ORGANISM: ARTIFICIAL
<220> FEATURE:
<223> OTHER INFORMATION: CDR-L2 VARIANT 3

<400> SEQUENCE: 107

Leu Ala Thr Asn Leu Glu Ser
1               5

<210> SEQ ID NO 108
<211> LENGTH: 7
<212> TYPE: PRT
<213> ORGANISM: ARTIFICIAL
<220> FEATURE:
<223> OTHER INFORMATION: CDR-L2 VARIANT 4

<400> SEQUENCE: 108

Leu Ala Ser Asn Leu Lys Ser
1               5

<210> SEQ ID NO 109
<211> LENGTH: 7
<212> TYPE: PRT
<213> ORGANISM: ARTIFICIAL
<220> FEATURE:
<223> OTHER INFORMATION: CDR-L2 VARIANT 5

<400> SEQUENCE: 109

Leu Ala Ser Asn Leu Glu Lys
1               5

<210> SEQ ID NO 110
<211> LENGTH: 7
<212> TYPE: PRT
<213> ORGANISM: ARTIFICIAL
<220> FEATURE:
<223> OTHER INFORMATION: CDR-L2 VARIANT 6

<400> SEQUENCE: 110

Leu Ala Ser Arg Leu Glu Ser
1               5

<210> SEQ ID NO 111
```

```
<211> LENGTH: 7
<212> TYPE: PRT
<213> ORGANISM: ARTIFICIAL
<220> FEATURE:
<223> OTHER INFORMATION: CDR-L2 VARIANT 7

<400> SEQUENCE: 111

Leu Ala Ser Asn Leu His Ser
1               5

<210> SEQ ID NO 112
<211> LENGTH: 7
<212> TYPE: PRT
<213> ORGANISM: ARTIFICIAL
<220> FEATURE:
<223> OTHER INFORMATION: CDR-L2 VARIANT 8

<400> SEQUENCE: 112

Leu Ala Ser Asn Leu Ser Ser
1               5

<210> SEQ ID NO 113
<211> LENGTH: 7
<212> TYPE: PRT
<213> ORGANISM: ARTIFICIAL
<220> FEATURE:
<223> OTHER INFORMATION: CDR-L2 VARIANT 9

<400> SEQUENCE: 113

Leu Ala Ser Phe Leu Glu Ser
1               5

<210> SEQ ID NO 114
<211> LENGTH: 7
<212> TYPE: PRT
<213> ORGANISM: ARTIFICIAL
<220> FEATURE:
<223> OTHER INFORMATION: CDR-L2 VARIANT 10

<400> SEQUENCE: 114

Leu Ala Asn Asn Leu Glu Ser
1               5

<210> SEQ ID NO 115
<211> LENGTH: 9
<212> TYPE: PRT
<213> ORGANISM: ARTIFICIAL
<220> FEATURE:
<223> OTHER INFORMATION: CDR-L3 228B/C

<400> SEQUENCE: 115

Gln Gln Asn Asn Glu Asp Pro Arg Thr
1               5

<210> SEQ ID NO 116
<211> LENGTH: 9
<212> TYPE: PRT
<213> ORGANISM: ARTIFICIAL
<220> FEATURE:
<223> OTHER INFORMATION: CDR-L3 VARIANT 1

<400> SEQUENCE: 116

Gln Gln Asn Ala Glu Asp Pro Arg Thr
1               5

<210> SEQ ID NO 117
<211> LENGTH: 5
```

```
<212> TYPE: PRT
<213> ORGANISM: ARTIFICIAL
<220> FEATURE:
<223> OTHER INFORMATION: CDR-H1 228B/C

<400> SEQUENCE: 117

Ala Tyr Ser Val Asn
1               5

<210> SEQ ID NO 118
<211> LENGTH: 5
<212> TYPE: PRT
<213> ORGANISM: ARTIFICIAL
<220> FEATURE:
<223> OTHER INFORMATION: CDR-H1 VARIANT 1

<400> SEQUENCE: 118

Ala Lys Ser Val Asn
1               5

<210> SEQ ID NO 119
<211> LENGTH: 5
<212> TYPE: PRT
<213> ORGANISM: ARTIFICIAL
<220> FEATURE:
<223> OTHER INFORMATION: CDR-H1 VARIANT 2

<400> SEQUENCE: 119

Ala Asn Ser Val Asn
1               5

<210> SEQ ID NO 120
<211> LENGTH: 5
<212> TYPE: PRT
<213> ORGANISM: ARTIFICIAL
<220> FEATURE:
<223> OTHER INFORMATION: CDR-H1 VARIANT 3

<400> SEQUENCE: 120

Gly Tyr Ser Val Asn
1               5

<210> SEQ ID NO 121
<211> LENGTH: 5
<212> TYPE: PRT
<213> ORGANISM: ARTIFICIAL
<220> FEATURE:
<223> OTHER INFORMATION: CDR-H1 VARIANT 4

<400> SEQUENCE: 121

Ala His Ser Val Asn
1               5

<210> SEQ ID NO 122
<211> LENGTH: 5
<212> TYPE: PRT
<213> ORGANISM: ARTIFICIAL
<220> FEATURE:
<223> OTHER INFORMATION: CDR-H1 VARIANT 5

<400> SEQUENCE: 122

Ala Arg Ser Val Asn
1               5

<210> SEQ ID NO 123
<211> LENGTH: 16
<212> TYPE: PRT
```

```
<213> ORGANISM: ARTIFICIAL
<220> FEATURE:
<223> OTHER INFORMATION: CDR-H2 228B/C

<400> SEQUENCE: 123

Met Ile Trp Gly Asp Gly Lys Ile Val Tyr Asn Ser Ala Leu Lys Ser
1               5                   10                  15

<210> SEQ ID NO 124
<211> LENGTH: 16
<212> TYPE: PRT
<213> ORGANISM: ARTIFICIAL
<220> FEATURE:
<223> OTHER INFORMATION: CDR-H2 VARIANT 1

<400> SEQUENCE: 124

Met Ile Trp Gly Asp Gly Lys Ile Ser Tyr Asn Ser Ala Leu Lys Ser
1               5                   10                  15

<210> SEQ ID NO 125
<211> LENGTH: 16
<212> TYPE: PRT
<213> ORGANISM: ARTIFICIAL
<220> FEATURE:
<223> OTHER INFORMATION: CDR-H2 VARIANT 2

<400> SEQUENCE: 125

Met Ile Trp Gly Asp Gly Lys Ile Val Tyr Asn Ser Ala Leu Glu Ser
1               5                   10                  15

<210> SEQ ID NO 126
<211> LENGTH: 16
<212> TYPE: PRT
<213> ORGANISM: ARTIFICIAL
<220> FEATURE:
<223> OTHER INFORMATION: CDR-H2 VARIANT 3

<400> SEQUENCE: 126

Met Ile Trp Gly Asp Gly Lys Ile Val Tyr Asn Ser Ala Leu Lys Ser
1               5                   10                  15

<210> SEQ ID NO 127
<211> LENGTH: 16
<212> TYPE: PRT
<213> ORGANISM: ARTIFICIAL
<220> FEATURE:
<223> OTHER INFORMATION: CDR-H2 VARIANT 4

<400> SEQUENCE: 127

Met Ile Trp Gly Asp Gly Lys Ile Val Tyr Asn Ser Asp Leu Lys Ser
1               5                   10                  15

<210> SEQ ID NO 128
<211> LENGTH: 16
<212> TYPE: PRT
<213> ORGANISM: ARTIFICIAL
<220> FEATURE:
<223> OTHER INFORMATION: CDR-H2 VARIANT 5

<400> SEQUENCE: 128

Met Ile Trp Gly Asp Gly Lys Val Val Tyr Asn Ser Ala Leu Lys Ser
1               5                   10                  15

<210> SEQ ID NO 129
<211> LENGTH: 16
<212> TYPE: PRT
<213> ORGANISM: ARTIFICIAL
```

```
<220> FEATURE:
<223> OTHER INFORMATION: CDR-H2 VARIANT 6

<400> SEQUENCE: 129

Met Ile Trp Gly Asp Gly Lys Ile Val Tyr Asn Ser Glu Leu Lys Ser
1               5                   10                  15

<210> SEQ ID NO 130
<211> LENGTH: 16
<212> TYPE: PRT
<213> ORGANISM: ARTIFICIAL
<220> FEATURE:
<223> OTHER INFORMATION: CDR-H2 VARIANT 7

<400> SEQUENCE: 130

Met Ile Trp Gly Asp Gly Lys Ile Ala Tyr Asn Ser Ala Leu Lys Ser
1               5                   10                  15

<210> SEQ ID NO 131
<211> LENGTH: 16
<212> TYPE: PRT
<213> ORGANISM: ARTIFICIAL
<220> FEATURE:
<223> OTHER INFORMATION: CDR-H2 VARIANT 8

<400> SEQUENCE: 131

Met Ile Trp Gly Asp Gly Lys Ile Val Tyr Asn Ser Ala Leu Lys Glu
1               5                   10                  15

<210> SEQ ID NO 132
<211> LENGTH: 16
<212> TYPE: PRT
<213> ORGANISM: ARTIFICIAL
<220> FEATURE:
<223> OTHER INFORMATION: CDR-H2 VARIANT 9

<400> SEQUENCE: 132

Met Val Trp Gly Asp Gly Lys Ile Val Tyr Asn Ser Ala Leu Lys Ser
1               5                   10                  15

<210> SEQ ID NO 133
<211> LENGTH: 16
<212> TYPE: PRT
<213> ORGANISM: ARTIFICIAL
<220> FEATURE:
<223> OTHER INFORMATION: CDR-H2 VARIANT 10

<400> SEQUENCE: 133

Met Ile Trp Gly Asp Gly Lys Ile Val Tyr Asn Ser Ala Leu Ala Ser
1               5                   10                  15

<210> SEQ ID NO 134
<211> LENGTH: 16
<212> TYPE: PRT
<213> ORGANISM: ARTIFICIAL
<220> FEATURE:
<223> OTHER INFORMATION: CDR-H2 VARIANT 11

<400> SEQUENCE: 134

Met Ile Trp Gly Asp Gly Lys Lys Val Tyr Asn Ser Ala Leu Lys Ser
1               5                   10                  15

<210> SEQ ID NO 135
<211> LENGTH: 10
<212> TYPE: PRT
<213> ORGANISM: ARTIFICIAL
<220> FEATURE:
```

<223> OTHER INFORMATION: CDR-H3 228B/C

<400> SEQUENCE: 135

Asp Gly Tyr Tyr Pro Tyr Ala Met Asp Asn
1               5                   10

<210> SEQ ID NO 136
<211> LENGTH: 10
<212> TYPE: PRT
<213> ORGANISM: ARTIFICIAL
<220> FEATURE:
<223> OTHER INFORMATION: CDR-H3 VARIANT 1

<400> SEQUENCE: 136

Asp Gly Arg Tyr Pro Tyr Ala Met Asp Asn
1               5                   10

<210> SEQ ID NO 137
<211> LENGTH: 10
<212> TYPE: PRT
<213> ORGANISM: ARTIFICIAL
<220> FEATURE:
<223> OTHER INFORMATION: CDR-H3 VARIANT 2

<400> SEQUENCE: 137

Asp Gly Tyr Tyr Pro Tyr Ala Met Lys Asn
1               5                   10

<210> SEQ ID NO 138
<211> LENGTH: 10
<212> TYPE: PRT
<213> ORGANISM: ARTIFICIAL
<220> FEATURE:
<223> OTHER INFORMATION: CDR-H3 VARIANT 3

<400> SEQUENCE: 138

Asp Gly Arg Tyr Pro Tyr Ala Met Lys Asn
1               5                   10

<210> SEQ ID NO 139
<211> LENGTH: 10
<212> TYPE: PRT
<213> ORGANISM: ARTIFICIAL
<220> FEATURE:
<223> OTHER INFORMATION: CDR-H3 VARIANT 4

<400> SEQUENCE: 139

Asp Gly Tyr Tyr Pro Tyr Ala Met Ser Asn
1               5                   10

<210> SEQ ID NO 140
<211> LENGTH: 10
<212> TYPE: PRT
<213> ORGANISM: ARTIFICIAL
<220> FEATURE:
<223> OTHER INFORMATION: CDR-H3 VARIANT 5

<400> SEQUENCE: 140

Asp Gly Tyr Tyr Pro Tyr Ala Met Ala Asn
1               5                   10

<210> SEQ ID NO 141
<211> LENGTH: 10
<212> TYPE: PRT
<213> ORGANISM: ARTIFICIAL
<220> FEATURE:
<223> OTHER INFORMATION: CDR-H3 VARIANT 6

```
<400> SEQUENCE: 141

Asp Gly Tyr Tyr Pro Tyr Ala Leu Asp Asn
1               5                   10

<210> SEQ ID NO 142
<211> LENGTH: 112
<212> TYPE: PRT
<213> ORGANISM: ARTIFICIAL
<220> FEATURE:
<223> OTHER INFORMATION: VARIABLE LIGHT CHAIN OF CL-89

<400> SEQUENCE: 142

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

<210> SEQ ID NO 143
<211> LENGTH: 118
<212> TYPE: PRT
<213> ORGANISM: ARTIFICIAL
<220> FEATURE:
<223> OTHER INFORMATION: VARIABLE HEAVY CHAIN CL-276G

<400> SEQUENCE: 143

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
                20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 144
<211> LENGTH: 112
<212> TYPE: PRT
<213> ORGANISM: ARTIFICIAL
<220> FEATURE:
<223> OTHER INFORMATION: VARIABLE LIGHT CHAIN OF RL-36
```

```
<400> SEQUENCE: 144

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

<210> SEQ ID NO 145
<211> LENGTH: 118
<212> TYPE: PRT
<213> ORGANISM: ARTIFICIAL
<220> FEATURE:
<223> OTHER INFORMATION: VARIABLE HEAVY CHAIN RL-36

<400> SEQUENCE: 145

Gln Val Thr Leu Arg Glu Ser Gly Pro Ala Leu Val Lys Pro Thr Gln
1               5                   10                  15

Thr Leu Thr Leu Thr Cys Thr Gly Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Asp Asn Trp Gly Gln Gly Ser
            100                 105                 110

Leu Val Thr Val Ser Ser
        115

<210> SEQ ID NO 146
<211> LENGTH: 118
<212> TYPE: PRT
<213> ORGANISM: ARTIFICIAL
<220> FEATURE:
<223> OTHER INFORMATION: VARIABLE HEAVY CHAIN RL-19

<400> SEQUENCE: 146

Gln Val Thr Leu Arg Glu Ser Gly Pro Ala Leu Val Lys Pro Thr Gln
1               5                   10                  15

Thr Leu Thr Leu Thr Cys Thr Ser Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60
```

```
Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Leu Asp Gly Tyr Tyr Pro Tyr Ala Met Asp Asn Trp Gly Gln Gly Ser
            100                 105                 110

Leu Val Thr Val Ser Ser
        115

<210> SEQ ID NO 147
<211> LENGTH: 118
<212> TYPE: PRT
<213> ORGANISM: ARTIFICIAL
<220> FEATURE:
<223> OTHER INFORMATION: VARIABLE HEAVY CHAIN RL-11

<400> SEQUENCE: 147

Gln Val Thr Leu Arg Glu Ser Gly Pro Ala Leu Val Lys Pro Thr Gln
 1               5                   10                  15

Thr Leu Thr Leu Thr Cys Thr Thr Ser Gly Phe Ser Leu Ser Ala Tyr
                 20                  25                  30

Ser Val Asn Trp Ile Arg Gln Pro Pro Gly Lys Ala Leu Glu Trp Leu
             35                  40                  45

Ala Met Ile Trp Gly Asp Gly Lys Ile Val Tyr Asn Ser Ala Leu Lys
         50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Val Asp Gly Tyr Tyr Pro Tyr Ala Met Asp Asn Trp Gly Gln Gly Ser
            100                 105                 110

Leu Val Thr Val Ser Ser
        115

<210> SEQ ID NO 148
<211> LENGTH: 118
<212> TYPE: PRT
<213> ORGANISM: ARTIFICIAL
<220> FEATURE:
<223> OTHER INFORMATION: VARIABLE HEAVY CHAIN RL-8

<400> SEQUENCE: 148

Gln Val Thr Leu Arg Glu Ser Gly Pro Ala Leu Val Lys Pro Thr Gln
 1               5                   10                  15

Thr Leu Thr Leu Thr Cys Thr Leu Ser Gly Phe Ser Leu Ser Ala Tyr
                 20                  25                  30

Ser Val Asn Trp Ile Arg Gln Pro Pro Gly Lys Ala Leu Glu Trp Leu
             35                  40                  45

Ala Met Ile Trp Gly Asp Gly Lys Ile Val Tyr Asn Ser Ala Leu Lys
         50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Ser Asp Gly Tyr Tyr Pro Tyr Ala Met Asp Asn Trp Gly Gln Gly Ser
            100                 105                 110

Leu Val Thr Val Ser Ser
        115
```

<210> SEQ ID NO 149
<211> LENGTH: 118
<212> TYPE: PRT
<213> ORGANISM: ARTIFICIAL
<220> FEATURE:
<223> OTHER INFORMATION: VARIABLE HEAVY CHAIN RL-45

<400> SEQUENCE: 149

Gln Val Thr Leu Arg Glu Ser Gly Pro Ala Leu Val Lys Pro Thr Gln
1               5                   10                  15

Thr Leu Thr Leu Thr Cys Thr Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Thr Asp Gly Tyr Tyr Pro Tyr Ala Met Asp Asn Trp Gly Gln Gly Ser
            100                 105                 110

Leu Val Thr Val Ser Ser
        115

<210> SEQ ID NO 150
<211> LENGTH: 112
<212> TYPE: PRT
<213> ORGANISM: ARTIFICIAL
<220> FEATURE:
<223> OTHER INFORMATION: VARIABLE LIGHT CHAIN RL-36-L1,59

<400> SEQUENCE: 150

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Gln Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

<210> SEQ ID NO 151
<211> LENGTH: 118
<212> TYPE: PRT
<213> ORGANISM: ARTIFICIAL
<220> FEATURE:
<223> OTHER INFORMATION: VARIABLE HEAVY CHAIN RL36-L1,59

<400> SEQUENCE: 151

Gln Val Thr Leu Arg Glu Ser Gly Pro Ala Leu Val Lys Pro Thr Gln
1               5                   10                  15

```
Thr Leu Thr Leu Thr Cys Thr Gly Ser Gly Phe Ser Leu Ser Ala Tyr
            20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
        50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Val Asp Gly Tyr Tyr Pro Tyr Ala Met Asp Asn Trp Gly Gln Gly Ser
            100                 105                 110

Leu Val Thr Val Ser Ser
            115

<210> SEQ ID NO 152
<211> LENGTH: 248
<212> TYPE: PRT
<213> ORGANISM: ARTIFICIAL
<220> FEATURE:
<223> OTHER INFORMATION: SINGLE CHAIN FV

<400> SEQUENCE: 152

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
        50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser Gly Gly Ser Arg Ser Ser Ser Ser Gly
            115                 120                 125

Gly Gly Gly Ser Gly Gly Gly Asp Ile Val Met Thr Gln Ser Pro
        130                 135                 140

Asp Ser Leu Ser Val Ser Leu Gly Glu Arg Ala Thr Ile Asn Cys Arg
145                 150                 155                 160

Ala Ser Lys Ser Val Asp Ser Tyr Gly Asn Ser Phe Met His Trp Tyr
            165                 170                 175

Gln Gln Lys Pro Gly Gln Pro Pro Lys Leu Leu Ile Tyr Leu Ala Ser
            180                 185                 190

Asn Leu Glu Ser Gly Val Pro Asp Arg Phe Ser Gly Ser Gly Ser Gly
            195                 200                 205

Thr Asp Phe Thr Leu Thr Ile Ser Ser Val Gln Ala Glu Asp Val Ala
            210                 215                 220

Val Tyr Tyr Cys Gln Gln Asn Asn Glu Asp Pro Arg Thr Phe Gly Gly
225                 230                 235                 240

Gly Thr Lys Val Glu Ile Lys Arg
            245
```

TREATMENT OF CANCER WITH A NOVEL ANTI-IL13 MONOCLONAL ANTIBODY

This application claims priority to U.S. Provisional Application No. 60/532,130, filed on 23 Dec. 2003.

BACKGROUND

IL13 is a pleiotropic TH2 cytokine produced predominantly by $CD4^+$ T-helper type 2 cells, as well as NKT cells, basophils, and mast cells (Hershey, G K K, J Allergy Clin Immunol. (2003) 111: 677-90). In addition to its etiologic roles in asthma, fibrosis, chronic pulmonary obstructive disease and ulcerative colitis Wynn, T A, Annu Rev Immunol. (2003) 21: 425-56; Wynn T A., Nat Rev Immunol. (2004) 4: 583-94; Heller F et al., Immunity (2002) 17: 629-38), IL13 is also known to play important roles in tumor growth (Kapp U et al., J Exp Med. (1999) 189: 1939-4; Trieu Y et al., Cancer Res. 2004; 64: 3271-5) and modulation of tumor immunity (Terabe M et al., Cancer Immunol Immunother. 2004; 53: 79-85; Terabe M et al., Nat Immunol. 2000; 1: 515-20). Therefore, IL13 and its receptors are potential therapeutic targets for cancer.

Hodgkin's lymphoma (HL) is a malignant disorder of the lymph nodes characterized by the abnormal production of multiple cytokines from the malignant cell population of HL, the Reed-Sternberg (RS) cells (See Kapp et al. and Trieu et al., supra). IL13 was shown to promote HL proliferation by an autocrine mechanism. Anti-IL13 neutralizing monoclonal antibodies (MAbs) were shown to inhibit the proliferation of HL cells in vitro (Trieu et al. supra).

Accumulating evidence indicates that IL13 receptors are highly expressed on a variety of human malignant tumor cell lines (e.g., glioblastoma, head-and-neck tumors, squamous cell carcinoma, renal cell carcinoma, AIDS-associated Kaposi's carcinoma, prostate carcinoma, pancreatic carcinoma, and epithelial carcinomas such as adenocarcinoma of stomach, colon, and skin) (See e.g., Debinski W et al. J Biol Chem. (1995) 270: 16775-80; Puri R K et al. Blood (1996) 87: 4333-9; Maini A et al. J Urol. (1997) 158: 948-53; Debinski W et al. Clin Cancer Res. (1995) 1: 1253-8; Kornmann M et al. Anticancer Res. (1999) 19: 125-31; Husain S R et al. Blood (2000) 95: 3506-13; Kawakami K et al. Cancer Res. (2001) 61: 6194-6200). A recombinant fusion protein comprising IL13 coupled to a mutated form of Pseudomonas exotoxin was shown to specifically kill these tumor cells in vitro. Therefore, these data suggest that the IL13 receptor is an attractive target for directing selective tumor killing.

It is now known that the major mediators of anti-tumor immunity are $CD4^+$ TH1 cells and $CD8^+$ cytotoxic T lymphocytes (CTL). Since immune deviation toward TH2 suppresses TH1 development, it has been suggested that induction of a TH2 response in cancer patients is one of the major mechanisms repressing tumor immunosurveillance. Terabe et al. showed that an IL13 inhibitor (sIL13R□2-Fc) inhibited tumor recurrence in a Mouse model. Similar observations were also found with STAT6 or IL4R knockout mice, but not with IL4 knockout mice. Together, these results indicate that IL13 plays an important role in suppressing anti-tumor immunity in vivo. Therefore, inhibiting IL13 could promote anti-tumor immunity in cancer patients.

Antibody-based therapy has proved very effective in the treatment of various cancers. For example, HERCEPTIN® and RITUXAN® have been used successfully to treat breast cancer and non-Hodgkin's lymphoma, respectively. The present invention provides alternative methods of treating cancer that overcome the limitations of conventional therapeutic methods as well as offer additional advantages that will be apparent from the detailed description below.

SUMMARY OF THE INVENTION

The present application relates to the treatment of cancers and/or tumors expressing IL13, with novel anti-IL13 monoclonal antibodies. The antibodies useful In the present invention comprise novel anti-IL13 antibodies that bind specifically and with high affinity to both glycosylated and non-glycosylated human IL13; do not bind mouse IL13, and neutralize human IL13 activity at an approximate molar ratio of 1:2 (MAb:IL13). Also included in the present invention are antibodies comprising the antigen binding regions derived from the light and/or heavy chain variable regions of said antibodies. The antibodies of the invention may be monoclonal, and a monoclonal antibody may be a human antibody, a chimeric antibody, or a humanized antibody.

Examples of these antibodies are 228B/C-1, 228A-4, 227-26, and 227-43. The hybridomas that produce these antibodies were deposited on Nov. 20, 2003, with the American Type Culture Collection, 10801 University Blvd., Manassas, Va. 20110-2209, under Accession Numbers PTA-5657, PTA-5656, PTA-5654, and PTA-5655, respectively. These antibodies can target an IL13-expressing tumor cell in vivo. These antibodies are described in a co-pending application (WO 2005/062972, filed 23 Dec. 2004) and incorporated herein by reference.

Antibodies useful in the present invention also include antibodies having a VL sequence at least 95% homologous to that set forth in SEQ ID NO: 3, and a VH sequence at least 95% homologous to that set forth in SEQ ID NO: 4; antibodies which have a VL sequence at least 95% homologous to that set forth in SEQ ID NO: 5, and a VH sequence at least 95% homologous to that set forth in SEQ ID NO: 6; and antibodies which have a VL sequence at least 95% homologous to that set forth in SEQ ID NO: 7, and a VH sequence at least 95% homologous to that set forth in SEQ ID NO: 8. The present invention also includes a recombinant antibody molecule, or an IL13-binding fragment thereof, comprising at least one antibody heavy chain, or an IL13-binding fragment thereof, comprising non-human CDRs at positions 31-35 (CDR1), 50-65 (CDR2) and 95-102 (CDR3) (Kabat numbering) from a mouse anti-IL13 antibody, wherein positions 27-30 have the amino acid Gly 26, Phe 27, Ser 28, Leu 29, Asn 30, (SEQ ID NO: 18); and at least one antibody light chain, or an IL13-binding fragment thereof, comprising non-human CDRs at positions 24-34 (CDR1), 50-56 (CDR2) and 89-97 (CDR3) from a mouse anti-IL13 antibody, and framework regions from a human monoclonal antibody.

Antibodies useful in the present invention also include human antigen-binding antibody fragments of the antibodies of the present invention including, but are not limited to, Fab, Fab' and $F(ab')_2$, Fd, single-chain Fvs (scFv), single-chain antibodies, disulfide-linked Fvs (sdFv). The invention also includes single-domain antibodies comprising either a VL or VH domain. On example is an scFv having the sequence as set forth in SEQ ID NO 152.

Antibodies also useful in the present invention include humanized sequences of monoclonal antibody 228B/C-1. These humanized recombinant antibody molecules comprise a variable light chain region comprising an amino acid sequence having the formula: FRL1-CDRL1-FRL2-CDRL2-FRL3-CDRL3-FRL4, wherein FRL1 consists of any one of SEQ ID Nos: 20-25; CDRL1 consists of any one of SEQ ID NOs: 99-103; FR1 consists of SEQ ID NO: 29; CDRL2 consists of any one of SEQ ID NOs: 104-114; FRL3 consists of any one of SEQ ID NOs: 30-56; CDRL3 consists of any of SEQ ID NOs: 115-116; and FRL4 consists of SEQ ID NO: 57-59; and comprising a variable heavy chain region comprising an amino acid sequence having the formula: FRH1-CDRH1-FRH2-CDRH2-FRH3-CDRH3-FRH4, wherein FRH1 consists of any one of SEQ ID NOs: 60-66; CDRH1 consists of any one of SEQ ID NOs: 117-122; FRH2 consists of any one of SEQ ID NOs: 67-75; CDRH2 consists of any one of SEQ ID NOs: 123-134; FRH3 consists of any one of SEQ ID NOs: 76-90; CDRH3 consists of any of SEQ ID NOs: 135-141; and FRH4 consists of SEQ ID NO: 91-92. The variable heavy chain region may further comprise at least the CH1 domain of a constant region or the CH1, CH2 and CH3 domains of a constant region. The heavy chain constant region may comprise an IgG antibody, wherein the IgG antibody is an IgG1 antibody, an IgG2 antibody, an IgG3 antibody, or an IgG4 antibody.

Additionally, antibodies included comprise recombinant antibody molecules wherein the variable light chain is chosen from any one of SEQ ID Nos: 3, 5, 7, 93, 95, 97, 142, 144, and 150, and a variable heavy chain chosen from any one of SEQ ID Nos: 4, 6, 8, 94, 96, 98, 143, 145, 146, 147, 148, and 149. One particular antibody comprises the variable light chain having the sequence set forth in SEQ ID NO: 142, and a variable heavy chain having the sequence set forth in SEQ ID NO: 143.

The binding epitope of MAb 228B/C-1 was mapped to a unique site on IL13 responsible for the interaction with IL4Rα, which constitutes part of the multimeric IL13R complex. This binding site on IL13 is distant from the site responsible for IL13R interaction, and therefore, 228B/C-1 can bind to IL13 bound on tumor cells overexpressing IL13R. Also provided are antibodies that compete for binding to the same epitope recognized by any of the aforementioned monoclonal antibodies. The present invention also includes antibodies that bind the same epitope as 228B/C-1. Epitope peptides include a peptide comprising essentially or consisting of ESLINVSG (SEQ ID NO: 18) or YCMLESLINVS (SEQ ID NO: 19).

In another embodiment, an isolated anti-IL13 monoclonal antibody that inhibits the growth of IL13-expressing cancer cells in vivo, or is cytotoxic in vivo, to such cells and tumors containing such cells, is provided. The invention provides anti-IL13 antibodies that are conjugated to a cytotoxic agent or to a growth inhibitory agent. The cytotoxic agent can be a toxin, cytotoxic small-molecule drug, high-energy radioactive isotope, photoactivable drug, pro-apoptotic protein or drug, cytolytic or nucleolytic enzyme.

Antibodies useful in the present invention may comprise a constant region of human IgG1, which can mediate tumor cell killing by complement-mediated cytolysis (CMC) and antibody-dependent cell-mediated cytotoxicity (ADCC). Such an antibody can alto suppress the growth of tumors which is IL13-dependent.

The anti-IL13 antibodies of the preceding embodiments include intact (full length) antibodies as well as antibody fragments. In one embodiment, the anti-IL13 antibody of any of the preceding embodiments is a chimeric, humanized or human antibody. human antigen-binding antibody fragments of the antibodies of the present invention including, but are not limited to, Fab, Fab' and F(ab')$_2$, Fd, single-chain Fvs (scFv), single-chain antibodies, disuffide-linked Fvs (sdFv). The invention also includes single-domain antibodies comprising either a VL or VH domain. On example is an scFv having the sequence of SEQ ID NO 152.

The invention also encompasses the use of a composition comprising any one of the anti-IL13 antibodies of the above embodiments, and a carrier, in the methods of the present invention. The carrier is a pharmaceutically-acceptable carrier. These compositions can be provided in an article of manufacture or a kit for the treatment of cancer.

Yet a separate aspect of the invention is a method of killing an IL13-expressing cancer cell, comprising contacting the cancer cell with an anti-IL13 antibody of any of the above embodiments, thereby killing the cancer cell. Another aspect is a method of alleviating or treating an IL13-expressing cancer in a mammal, comprising administering a therapeutically effective amount of the anti-IL13 antibodies of the invention to the mammal. In embodiments of the preceding methods, the cancer is renal cell carcinoma, glioma, brain tumors, Hodgkins lymphoma, or other tumors or cancers that express IL13 receptor on their surface. In a preferred embodiment of these methods, the anti-IL13 antibody is a human or a humanized antibody. In another preferred embodiment, the antibody is conjugated to a cytotoxic agent such as a toxin or a radioactive isotope and a cytostatic agent such as inhibitors to cyclin-dependent kinases.

The method of alleviating the IL13-expressing cancer anticipates administration of the anti-IL13 antibody in combination with other forms of cancer treatment, such as radiotherapy and chemotherapy. For the latter, the mammal is also receiving at least one chemotherapeutic agent. In a specific embodiment, the chemotherapeutic agent is wherein the chemotherapy is selected from the group of drugs such as but not limited to Doxorubicin, 5-Fluorouracil, Cytosine arabinoside, Cyclophosphamide, Thiotepa, Busulfan, Cytoxin, Taxot, Methotrexate, Cisplatin, Melphalan, Vinblastine, bleomycin and Carboplatin. In another specific embodiment, the anti-IL13 antibody can be used in conjunction with other anti-tumor antibodies such as, but not limited to, anti-VEGF MAb, anti-Her2 MAb, anti-EGFR MAb, anti-EpCam MAb, anti-ganglioside MAb, anti-tissue factor MAb and anti-integrin MAb.

In a further aspect, the invention provides an article of manufacture comprising a container and a composition contained therein, wherein the composition comprises an anti-IL13 antibody of the above embodiments, and further comprising a package insert indicating that the composition can be used to alleviate or treat a IL13-expressing cancer.

Another aspect of the invention comprises diagnosing a cancer or tumor overexpressing IL13 comprising the use of the anti-IL13 antibodies of the present invention to detect overexpression of IL13 in the biological sample taken from a patient suspected of having said cancer or tumor.

BRIEF DESCRIPTION OF FIGURES

FIG. 8 depicts the amino acid sequences of the VH and VL regions of monoclonal antibody 228B/C-1.

FIG. 9 depicts the amino acid sequences of the VH and VL regions of several humanized antibodies derived from monoclonal antibody 228 B/C-1

DETAILED DESCRIPTION

Figure 1:
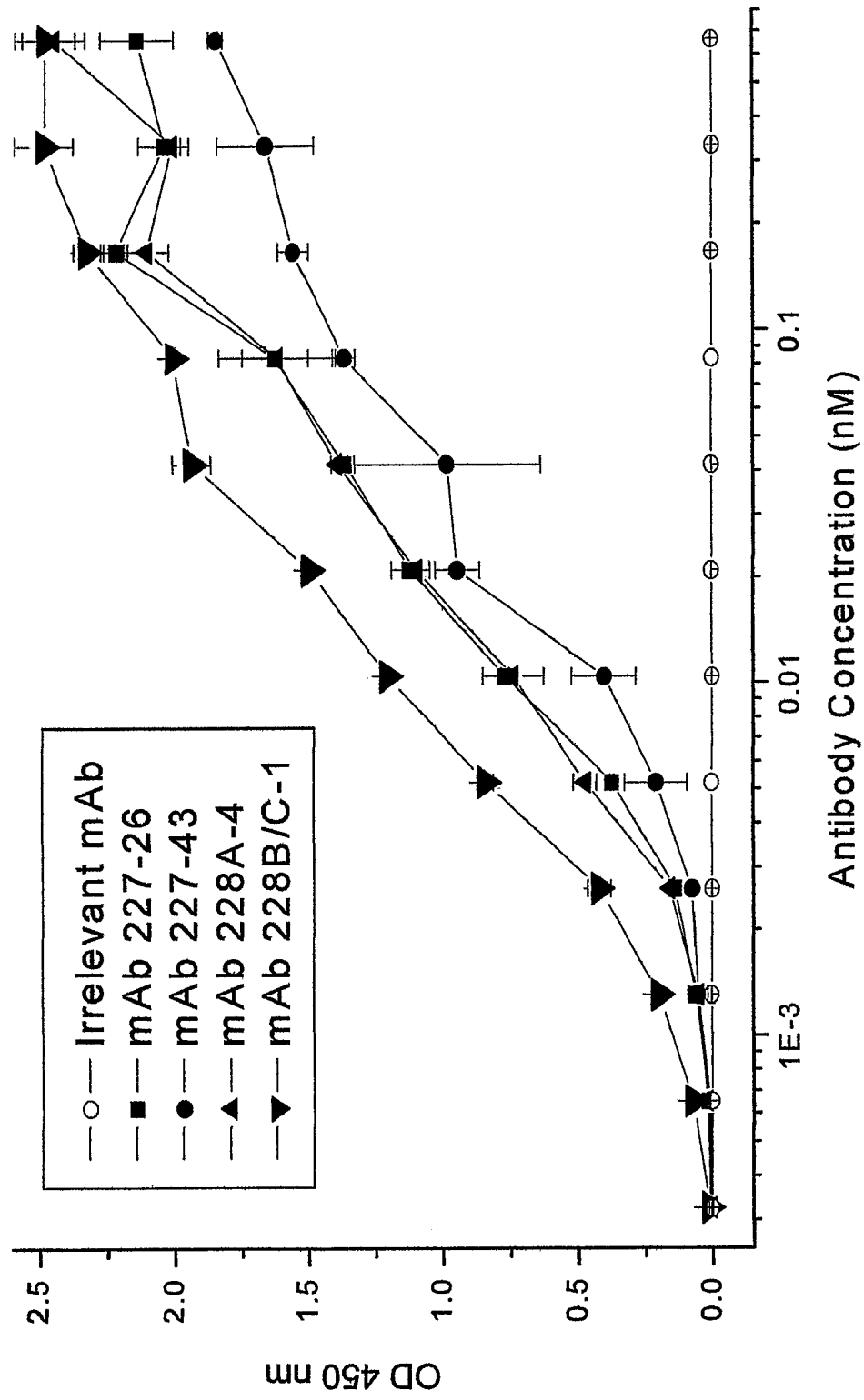
FIG. 1 depicts the binding of anti-IL13 monoclonal antibodies to human IL13.

This invention is not limited to the particular methodology, protocols, cell lines, vectors, or reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise, e.g., reference to "a host cell" includes a plurality of such host cells.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue of prior invention.

The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, lgD, IgA and Igy), class (e.g., IgG1, IgG2, IgG3, IgG4, IgA1 and IgA2) or subclass of immunoglobulin molecule. Moreover, the term "antibody" (Ab) or "monoclonal antibody" (mAb) is meant to include intact molecules, as well as, antibody fragments (such as, for example, Fab and F(ab')$_2$ fragments) which are capable of specifically binding to protein. Fab and F(ab')$_2$ fragments lack the Fc fragment of intact antibody, clear more rapidly from the circulation of the animal or plant, and may have less non-specific tissue binding than an intact antibody (Wahl et al., J. Nucl. Med. 24:316-325 (1983)).

As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound to Fc gamma receptors (Fc☐Rs) present on certain cytotoxic cells (e.g. Natural Killer (NK) cells, neutrophils, and macrophages) enable these cytotoxic effector cells to bind specifically to an antigen-bearing target cell and subsequently kill the target cell with cellular enzymes or oxidative free radicals. The antibodies "arm" the cytotoxic cells and are required for such killing. The primary cells for mediating ADCC, NK cells, express FcγRIII only, whereas monocytes express FcγRI, FcγRII and FcγRIII. To assess ADCC activity of a molecule of interest, an in vitro ADCC assay, such as that described below, may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

Immunogen

Recombinant IL13 was used to immunize mice to generate the hybridomas that produce the monoclonal antibodies of the present invention. Recombinant IL13 is commercially available from a number of sources (see, e.g. R & D Systems, Minneapolis, Minn., PeproTech, Inc., N.J., and Sanofi Bio-Industries, Inc., Tervose, Pa.). Alternatively, a gene or a cDNA encoding IL13 may be cloned into a plasmid or other expression vector and expressed in any of a number of expression systems according to methods well known to those of skill in the art. Methods of cloning and expressing IL13 and the nucleic acid sequence for IL13 are well known (see, for example, U.S. Pat. No. 5,652,123). Because of the degeneracy of the genetic code, a multitude of nucleotide sequences encoding IL13 polypeptides may be produced. One may vary the nucleotide sequence by selecting combinations based on possible codon choices. These combinations are made in accordance with the standard triplet generic code as applied to the nucleotide sequence that codes for naturally occurring IL13 polypeptide and all such variations are to be considered. Any one of these polypeptides may be used in the immunization of an animal to generate antibodies that bind to IL13.

The immunogen IL13 polypeptide may, when beneficial, be expressed as a fusion protein that has the IL13 polypeptide attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the protein. Fusion segments may include, but are not limited to, immunoglobulin Fc regions, glutathione-S-transferase, β-galactosidase, a poly-histidine segment capable of binding to a divalent metal ion, and maltose binding protein.

A fusion protein comprising a mutant form of human IL13 was used to generate the antibodies of the present invention. This mutant form of IL13 contained a single mutation resulting in an inactive form of the protein (Thompson et al., J. Biol. Chem. 274: 2994 (1969)). In order to generate neutralizing antibodies with high affinity, the fusion protein comprised the mutant IL13 protein fused to an immunoglobulin Fc, specifically IgG1, and was expressed in a mammalian cell line such that the recombinant protein was naturally glycosylated. The Fc portion of the fusion protein may have provided a conformational structure that exposed a key epitope. The glycosylation may have increased the immunogenicity of the epitope, allowing the generation of antibodies to this particular epitope.

IL13 polypeptides expressed in *E. coli* lack glycosylation and the commercially available antibodies tested were generated using this protein. We tested these antibodies, e.g., R&D Systems and Pharmingen, and found that they do not cross react with the epitope bound by the antibodies of the present invention.

Antibody Generation

The antibodies of the present invention may be generated by any suitable method known in the art. The antibodies of the present invention may comprise polyclonal antibodies. Methods of preparing polyclonal antibodies are known to the skilled artisan (Harlow, et al., Antibodies: a Laboratory Manual, (Cold spring Harbor Laboratory Press, 2nd ed. (1988), which is hereby incorporated herein by reference in its entirety).

For example, an immunogen as described above may be administered to various host animals including, but not limited to, rabbits, mice, rats, etc., to induce the production of sera containing polyclonal antibodies specific for the antigen. The administration of the immunogen may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*. Additional examples of adjuvants which may be employed include the MPL-TDM adjuvant (monophosphoryl lipid A, synthetic trehalose dicorynomycolate). Immunization protocols are well known in the art in the art and may be performed by any method that elicits an immune response in the animal host chosen, Adjuvants are also well known in the art.

Typically, the immunogen (with or without adjuvant) is injected into the mammal by multiple subcutaneous or intraperitoneal injections, or intramuscularly or through IV. The immunogen may include an IL13 polypeptide, a fusion protein or variants thereof. Depending upon the nature of the polypeptides (i.e., percent hydrophobicity, percent hydrophilicity, stability, net charge, isoelectric point etc.), it may be useful to conjugate the immunogen to a protein known to be immunogenic in the mammal being immunized. Such conjugation includes either chemical conjugation by derivatizing active chemical functional groups to both the immunogen and the immunogenic protein to be conjugated such that a covalent bond is formed, or through fusion-protein based methodology, or other methods known to the skilled artisan. Examples of such immunogenic proteins include, but are not limited to, keyhole limpet hemocyanin, ovalbumin, serum albumin, bovine thyroglobulin, soybean trypsin inhibitor, and promiscuous T helper peptides. Various adjuvants may be used to increase the immunological response as described above.

The antibodies of the present invention comprise monoclonal antibodies. Monoclonal antibodies may be prepared using hybridoma technology, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, 2.sup.nd ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies include, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96), Such antibodies may be of any immunoglobulin class including IgG, IgM, IgE, IgA, IgD and any subclass thereof. The hybridoma producing the mAb of this invention may be cultivated in vitro or in vivo.

Using typical hybridoma techniques, a host such as a mouse, a humanized mouse, a mouse with a human immune system, hamster, rabbit, camel or any other appropriate host animal, is typically immunized with an immunogen to elicit lymphocytes that produce or are capable of producing antibodies that will specifically bind to IL13. Alternatively, lymphocytes may be immunized in vitro with the antigen.

Generally, in making antibody-producing hybridomas, either peripheral blood lymphocytes ("PBLs") are used if cells of human origin are desired, or spleen cells or lymph node cells are used if non-human mammalian sources are desired. The lymphocytes are then fused with an immortalized cell line using p suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), substances that prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines may also be used for the production of human monoclonal antibodies (Kozbor, J. Immunol., 133: 3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the IL13. The binding specificity of monoclonal antibodies produced by the hybridoma cells is determined by, e.g., immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody to IL13 can, for example, be determined by a Scatchard analysis (Munson et al., Anal. Biochem., 107:220 (1980)).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. The monoclonal antibodies secreted by the subclones may be isolated or purified from the culture medium by conventional immunoglobulin purification procedures such as, e.g., protein A-sepharose, hydroxyapatite chromatography, gel exclusion chromatography, gel electrophoresis, dialysis, or affinity chromatography.

A variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as NS0 cells, Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety.

Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties). Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/60433, WO 98/24893, WO 98/16664, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,886,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human mAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards IL13, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are well known. Traditionally, the recombinant production of bispecific antibodies is based on the co-expression of two immunoglobulin heavy-chain/light-chain pairs, where the two heavy chains have different specificities (Milstein and Cuello, Nature, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It may have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

In addition, one can generate single-domain antibodies to IL-13. Examples of this technology have been described in WO 9425591 for antibodies derived from Camelidae heavy chain Ig, as well in US20030130496 describing the isolation of single domain fully human antibodies from phage libraries.

Identification of Anti-IL13 Antibodies

The present invention provides antagonist monoclonal antibodies that inhibit and neutralize the action of IL13. In particular, the antibodies of the present invention bind to IL13 and inhibit the activation of the IL13 receptor complex. The antibodies of the present invention include the antibodies designated 228B/C-1, 228A-4, 227-26, and 227-43, and humanized clones of 228B/C-1 are disclosed. The present invention also includes antibodies that bind to the same epitope as monoclonal antibody 228B/C-1.

Candidate anti-IL13 antibodies were tested by enzyme linked immunosorbent assay (ELISA), Western immunoblotting, or other immunochemical techniques, Assays performed to characterize the individual antibodies included: (1) Inhibition of IL13-autocrine proliferation of Hodgkin's lymphoma cell lines HDLM-2 and L-1236; (2) Inhibition of IL13-induced STAT6 phosphorylation in THP-1 cells; and (3)

Inhibition of IL13-induced suppression of CD14 expression in primary human monocytes; and (4) Inhibition of IL13-induced up-regulation of CD23 expression on primary human monocytes. Experimental details are described in the Examples.

Antibodies of the invention include, but are not limited to, polyclonal, monoclonal, monovalent, bispecific, heteroconjugate, multispecific, human, humanized or chimeric antibodies, single chain antibodies, single-domain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above.

The antibodies may be human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and single-domain antibodies comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments comprising any combination of variable region(s) with a hinge region, CH1, CH2, and CH3 domains. The antibodies of the invention may be from any animal origin including birds and mammals. Preferably, the antibodies are human, non-human primates, rodents (e.g., mouse and rat), donkey, sheep, rabbit, goat, guinea pig, camel, horse, or chicken.

The antibodies of the present invention may be monospecific, bispecific, trispecific or of greater multispecificity. Multispecific antibodies may be specific for different epitopes of IL13 or may be specific for both IL13 as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present Invention may be described or specified in terms of the epitope(s) or portion(s), of IL13 which they recognize or specifically bind. The epitope(s) or polypeptide portion(s) may be specified as described herein, e.g., by N-terminal and C-terminal positions, by size in contiguous amino acid residues, or listed in the Tables and Figures.

Antibodies of the present invention may also be described or specified in terms of their cross-reactivity. Antibodies that bind IL13 polypeptides, which have at least 95%, at least 90%, at least 85%, at least 80%, at least 75%, at least 70%, at least 65%, at least 60%, at least 55%, and at least 50% identity (as calculated using methods known in the art and described herein) to IL-13 are also included in the present invention.

In specific embodiments, antibodies of the present invention cross-react with monkey homologues of human IL13 and the corresponding epitopes thereof. In a specific embodiment, the above-described cross-reactivity is with respect to any single specific antigenic or immunogenic polypeptide, or combination(s) of the specific antigenic and/or immunogenic polypeptides disclosed herein.

Further included in the present invention are antibodies which bind polypeptides encoded by polynucleotides which hybridize to a polynucleotide encoding IL13 under stringent hybridization conditions. Antibodies of the present invention may also be described or specified in terms of their binding affinity to a polypeptide of the invention. Preferred binding affinities include those with an equilibrium dissociation constant or $K_D$ from $10^{-8}$ to $10^{-15}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Further included in the present invention are antibodies that bind to the same epitope as the anti-IL13 antibodies of the present invention. To determine if an antibody can compete for binding to the same epitope as the epitope bound by the anti-IL13 antibodies of the present invention including the antibodies produced by the hybridomas deposited with the ATCC, a cross-blocking assay, e.g., a competitive ELISA assay, can be performed. In an exemplary competitive ELISA assay, IL13 coated on the wells of a microtiter plate is pre-incubated with or without candidate competing antibody and then the biotin-labeled anti-IL13 antibody of the invention is added. The amount of labeled anti-IL13 antibody bound to the IL13 antigen in the wells is measured using avidin-peroxidase conjugate and appropriate substrate. The antibody can be labeled with a radioactive or fluorescent label or some other detectable and measurable label. The amount of labeled anti-IL13 antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an anti-IL13 antibody of the invention if the candidate antibody can block binding of the IL13 antibody by at least 20%, preferably by at least 20-50%, even more preferably, by at least 50% as compared to the control performed in parallel in the absence of the candidate competing antibody. It will be understood that variations of this assay can be performed to arrive at the same quantitative value.

Vectors and Host Cells

In another aspect, the present invention provides vector constructs comprising a nucleotide sequence encoding the antibodies of the present invention and a host cell comprising such a vector. Standard techniques for cloning and transformation may be used in the preparation of cell lines expressing the antibodies of the present invention.

Recombinant expression vectors containing a nucleotide sequence encoding the antibodies of the present invention can be prepared using well known techniques. The expression vectors include a nucleotide sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and/or other appropriate sequences which control transcription and translation initiation and termination. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of the appropriate nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody. The signal peptide may be cleaved from the polypeptide upon secretion of antibody from the cell. Examples of such secretory signals are well known and include, e.g., those described in U.S. Pat. No. 5,698,435, U.S. Pat. No. 5,698,417, and U.S. Pat. No. 6,204,023.

Host cells useful in the present invention include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5 K promoter).

The vector may be a plasmid vector, a single or double-stranded phage vector, or a single or double-stranded RNA or DNA viral vector. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells. Cell-free translation systems may also be employed to produce the protein using RNAs derived from the present DNA constructs. Such vectors may include the nucleotide sequence encoding the constant region of the antibody molecule (see, e.g., PCT Publication WO 86/05807; PCT Publication WO 89/01036; and U.S. Pat. No. 6,122,464) and the variable domain of the antibody may be cloned into such a vector for expression of the entire heavy or light chain.

Prokaryotes useful as host cells in the present invention include gram negative or gram positive organisms such as *E. coli*, and *B. subtilis*. Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the pKK223-3 (Pharmacia Fine Chemicals, Uppsala, Sweden), pGEM1 (Promega Biotec, Madison, Wis., USA), and the pET (Novagen, Madison, Wis., USA) and pRSET (Invitrogen Corporation, Carlsbad, Calif., USA) series of vectors (Studier, F. W., J. Mol. Biol. 219: 37 (1991); Schoepfer, R. Gene 124: 83 (1993)). Promoter sequences commonly used for recombinant prokaryotic host cell expression vectors include T7, (Rosenberg, et al. Gene 66, 125-135 (1987)), β-lactamase (penicillinase), lactose promoter system (Chang et al., Nature 275:615, (1978); and Goeddel et al., Nature 281:544, (1979)), tryptophan (trp) promoter system (Goeddel et al., Nucl. Acids Res. 8:4057, (1980)), and tac promoter (Sambrook et al., 1990, Molecular Cloning, A Laboratory Manual, 2d Ed., Cold Spring Harbor Laboratory, Cold Spring Harbor, N.Y.)

Yeasts useful in the present invention include those from the genus *Saccharomyces, Pichia, Actinomycetes* and *Kluyveromyces*. Yeast vectors will often contain an origin of replication sequence from a 2µ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991). Other suitable promoters and vectors for yeast and yeast transformation protocols are well known in the art. Yeast transformation protocols are well known. One such protocol is described by Hinnen et al., Proc. Natl. Acad. Sci., 75:1929 (1978). The Hinnen protocol selects for Trp$^+$ transformants in a selective medium.

Mammalian or insect host cell culture systems may also be employed to express recombinant antibodies, e.g., Baculovirus systems for production of heterologous proteins. In an insect system, *Autographa californica* nuclear polyhedrosis virus (ACNPV) may be used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

NS0 or Chinese hamster ovary (CHO) cells for mammalian expression of the antibodies of the present invention may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are commercially available.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions to polynucleotides that encode an antibody of the present invention.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly $A^+$ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be Inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

Methods of Producing Anti-IL13 Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as E. coli, and eukaryotic cells are commonly used for the expression of a recombinant antibody molecule, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk, hgprt or aprt-cells, respectively. Also, antimetabolite resistance can be used as the basis of selection for the following genes: dhfr, which confers resistance to methotrexate (Wigler et al., Proc. Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G418 (Wu and Wu, Biotherapy 3:87-95 (1991)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N.Y. (1993); Kriegler, Gene Transfer and Expression, A Laboratory Manual, Stockton Press, N.Y. (1990); and in Chapters 12 and 13, Dracopoli et al. (eds), Current Protocols in Human Genetics, John Wiley & Sons, N.Y. (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" (DNA Cloning, Vol. 3. Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., Harbor et al., supra, and PCT publication WO 93/21232; EP 439,095; Naramura et al., Immunol. Lett. 39:91-99 (1994); U.S. Pat. No. 5,474,981; Gillies et al., Proc. Natl. Acad. Sci. 89:1428-1432 (1992); Fell et al., J. Immunol. 146:2446-2452 (1991), which are incorporated by reference in their entireties.

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Diagnostic Uses for Anti-IL13 Antibodies

The antibodies of the invention include derivatives that are modified, i.e., by the covalent attachment of any type of molecule to the antibody, such that covalent attachment does not interfere with binding to IL13. For example, but not by way of limitation, the antibody derivatives include antibodies that have been modified, e.g., by biotinylation, HRP, or any other detectable moiety.

Antibodies of the present invention may be used, for example, but not limited to, to detect the level of IL13 from a cancer patient, including both in vitro and in vivo diagnostic methods. For example, the antibodies may be used in immunoassays for qualitatively and quantitatively measuring levels of IL13 in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantiy fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays.

The present invention further encompasses antibodies or fragments thereof conjugated to a diagnostic agent. The antibodies can be used diagnostically to, for example, monitor the development or progression of cancer as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Labeled antibodies, and derivatives and analogs thereof, which specifically bind to IL13 can be used for diagnostic purposes to detect, diagnose, or monitor diseases, disorders, and/or conditions associated with the aberrant expression and/or activity of IL13. The invention provides for the detection of aberrant expression of IL13, comprising (a) assaying the expression of IL13 in cells or body fluid of an individual using one or more antibodies of the present invention specific to IL13 and (b) comparing the level of gene expression with a standard gene expression level, whereby an increase or decrease in the assayed IL13 expression level compared to the standard expression level is indicative of aberrant expression.

The invention provides a diagnostic assay for diagnosing a disorder, comprising (a) assaying the expression of IL13 in cells or body fluid of an individual using one or more antibodies of the present invention and (b) comparing the level of gene expression with a standard gene expression level, whereby an increase or decrease in the assayed gene expression level compared to the standard expression level is indicative of a particular disorder.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$-C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of IL13 in an animal, preferably a mammal and most preferably a human. In one embodiment, diagnosis comprises: a) administering (for example, parenterally, subcutaneously, or intraperitoneally) to a subject an effective amount of a labeled molecule which specifically binds to IL13; b) waiting for a time interval following the administration permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of IL13. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label, Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No.

5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

In another aspect, the present invention provides a method for diagnosing the predisposition of a patient to develop diseases caused by the unregulated expression of cytokines. Increased amounts of IL13 in certain patient cells, tissues, or body fluids may indicate that the patient is predisposed to certain diseases. In one embodiment, the method comprises collecting a cell, tissue, or body fluid sample a subject known to have low or normal levels of IL13, analyzing the tissue or body fluid for the presence of IL13 in the tissue, and predicting the predisposition of the patient to certain immune diseases based upon the level of expression of IL13 in the tissue or body fluid. In another embodiment, the method comprises collecting a cell, tissue, or body fluid sample known to contain a defined level of IL13 from a patient, analyzing the tissue or body fluid for the amount of IL13, and predicting the predisposition of the patient to certain diseases based upon the change in the amount of IL13 compared to a defined or tested level established for normal cell, tissue, or bodily fluid. The defined level of IL13 may be a known amount based upon literature values or may be determined in advance by measuring the amount in normal cell, tissue, or body fluids. Specifically, determination of IL13 levels in certain tissues or body fluids permits specific and early, preferably before disease occurs, detection of immune diseases in the patient. Immune diseases that can be diagnosed using the present method include, but are not limited to, the Immune diseases described herein. In the preferred embodiment, the tissue or body fluid is peripheral blood, peripheral blood leukocytes, biopsy tissues such as lung or skin biopsies, and tissue.

Therapeutic Uses of Anti-IL13 Antibodies

An antibody, with or without a therapeutic moiety conjugated to it, administered alone or in combination with cytotoxic or cytostatic factor(s) can be used as a therapeutic. The present invention is directed to antibody-based therapies which involve administering antibodies of the invention to an animal, a mammal, or a human, for treating an IL13-mediated disease, disorder, or condition. Antibodies directed against IL13 are useful for inhibiting tumors or cancer cell proliferation in animals, including but not limited to cows, pigs, horses, chickens, cats, dogs, non-human primates etc., as well as humans. For example, by administering a therapeutically acceptable dose of an antibody, or antibodies, of the present invention, or a cocktail of the present antibodies, or in combination with other antibodies of varying sources, cancers or tumors may be reduced or eliminated in the treated mammal.

Therapeutic compounds of the invention include, but are not limited to, antibodies of the invention (including fragments, analogs and derivatives thereof as described herein) and nucleic acids encoding antibodies of the invention as described below (including fragments, analogs and derivatives thereof and anti-idiotypic antibodies as described herein). The antibodies of the invention can be used to treat, inhibit or prevent diseases, disorders or conditions associated with aberrant expression and/or activity of IL13, including, but not limited to, any one or more of the diseases, disorders, or conditions described herein. The treatment and/or prevention of diseases, disorders, or conditions associated with aberrant expression and/or activity of IL13 includes, but are not limited to, alleviating symptoms associated with those diseases, disorders or conditions. Antibodies of the invention may be provided in pharmaceutically acceptable compositions as known in the art or as described herein.

Anti-IL13 antibodies of the present invention may be used therapeutically in a variety of diseases. The present invention provides a method for preventing or treating IL13-mediated diseases in a mammal. The method comprises administering a disease preventing or treating amount of anti-IL13 antibody to the mammal. The anti-IL13 antibody binds to IL13 and regulates cytokine and cellular receptor expression resulting in cytokine levels characteristic of non-disease states.

The amount of the antibody which will be effective in the treatment, inhibition and prevention of a disease or disorder associated with aberrant expression and/or activity of IL13 can be determined by standard clinical techniques. The antibody can be administered in treatment regimes consistent with the disease, e.g., a single or a few doses over one to several days to ameliorate a disease state or periodic doses over an extended time to prevent allergy or asthma. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patients body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The antibodies of this invention may be advantageously utilized in combination with other monoclonal or chimeric antibodies, or with lymphokines or hematopoietic growth factors (such as, e.g., IL-2, IL-3, IL-7, IFN, GCSF, GMCSF, Flt3, IL21) and unmethylated CpG containing oligonucleotides, for example, which serve to increase the number or activity of effector cells which interact with the antibodies.

The antibodies of the invention may be administered alone or in combination with other types of treatments, such as chemotherapy and radiotherapy.

In a preferred aspect, the antibody is substantially purified (e.g., substantially free from substances that limit its effect or produce undesired side-effects).

The anti-IL13 antibody can be administered to the mammal in any acceptable manner. Methods of introduction include but are not limited to intradermal, intramuscular, intraperitoneal, intravenous, subcutaneous, intranasal, epidural, inhalation and oral routes. The antibodies or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent. The antibody may also be administered into the lungs of a patient in the form of a dry powder composition (See e.g., U.S. Pat. No. 6,514,496).

In a specific embodiment, it may be desirable to administer the therapeutic antibodies or compositions of the invention locally to the area in need of treatment; this may be achieved by, for example, and not by way of limitation, local infusion, topical application, by injection, by means of a catheter, by means of a suppository, or by means of an implant, said implant being of a porous, non-porous, or gelatinous material, including membranes, such as sialastic membranes, or fibers. Preferably, when administering an antibody of the invention, care must be taken to use materials to which the protein does not absorb.

In another embodiment, the antibody can be delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the antibody can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target.

The present invention also provides pharmaceutical compositions. Such compositions comprise a therapeutically effective amount of the antibody, and a physiologically acceptable carrier. In a specific embodiment, the term "physiologically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable carriers are described in "Remington's Pharmaceutical Sciences" by E. W. Martin. Such compositions will contain an effective amount of the antibody, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In addition, the antibodies of the present invention may be conjugated to various effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387. An antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi, A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-68 (1982). Alternatively, an antibody can be conjugated to a second antibody to form an antibody heteroconjugate. (See, e.g., Segal in U.S. Pat. No. 4,676,980).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G, CSF"), or other growth factors.

EXAMPLES

Example 1

Preparation of IL13 Immunogen

A Mutated, Inactive Human IL13/Fc (MT-IL13/Fc)

A. Cloning and Construction of an Expression Plasmid for MT-IL13/Fc

It was reported that human IL13 with a mutation (glutamic acid to lysine) at amino acid residue #13 bound IL13Rα1 with equal or higher affinity but had lost the ability to activate IL13Rα1-bearing cells (Thompson et al., J. Biol. Chem., 274: 29944 (1999)). This mutated, inactive IL13, designated MT-IL13, was expressed in human embryonic kidney cells 293-T. The purified recombinant protein was used as the immunogen in the present invention to generate anti-IL13 monoclonal antibodies. Two oligonucleotide primers:

(SEQ ID NO 9)
5' AAGCTTTCCCCAGGCCCTGTGCCTCCCTCTACAGCCCTCAGGAAGCT CAT 3'

(SEQ ID NO 10)
5' CTCGAGGTTGAACCGTCCCTCGCGAAAAAG 3' corresponding to the oligonucleotide sequence of MT-IL13 gene were synthesized and used as templates in polymerase chain reactions (PCR) to clone the IL13 gene from human testis cDNA library (BD Biosciences Clontech, Palo Alto, Calif.). The PCR fragment (342 base pairs) which lacked the predicted signal peptide sequence of IL13 was ligated into the pSecTag/FRT vector (Invitrogen, Carlsbad, Calif.) that contained a secretion signal peptide sequence at the 5' end and a human Fcγ1 (hinge and constant regions CH2 and CH3) sequence at the 3' end. The construct's composition was confirmed by sequencing.

B. Producton of MT-IL13/Fc from Transfected 293T Cells

For transient expression of MT-IL13/Fc, purified plasmid DNA was transfected into 293T cells by Lipofectamine 2000 (Invitrogen), according to the manufacturer's protocol. At 72 hours post-transfection, culture supernatants from transfected cells were collected for purification. For stable expression of MT-IL13/Fc, cell lines were established using a Flp-In 293T cell line (Invitrogen). To confirm expression, culture supernatants were analyzed by sodium dodecyl sulfate polyacrylamide gel electrophoresis (SDS-PAGE). The separated proteins were transferred to nitrocellulose membrane and detected by reaction with horseradish peroxidase (HRP) conjugated mouse anti-human IgG (Fc) monoclonal antibody (Sigma, St. Louis, Mo.) or polyclonal goat anti-IL13 antibodies (R&D Systems, Minneapolis, Minn.), which were then detected with HRP-donkey anti-goat IgG (Jackson lmmunoResearch Laboratories, West Grove, Pa.). The immunoreactive proteins were identified on film, using enhanced chemi-luminescence detection (Supersignal West Pico Chemiluminescent Substrate, Pierce, Rockford, Ill.).

C. Purification of MTIL13/Fc

MT-IL13/Fc was purified with a hyper-D protein A affinity column (Invitrogen) equilibrated with phosphate-buffered saline (PBS). After applying the cell culture supernatant to the column, the resin was washed with more than 20 column volumes of PBS. Then, the resin was washed with SCC buffer (0.05 M sodium citrate, 0.5 M sodium chloride, pH 6.0) to remove unbound proteins. The IL13 fusion proteins were then eluted (0.05 M sodium citrate, 0.15 M sodium chloride, pH 3.0) and dialyzed in PBS.

Fractions from the affinity column containing MT-IL13/Fc were analyzed by SDS-PAGE. The purity of the proteins were analyzed by Coomassie Blue staining and the identity of the proteins by Western immunoblotting using goat anti-human IgG (Fc) antibody (Sigma) and goat anti-human IL13 antibody (R&D Systems) as described above.

Example 2

Generation of Anti-IL13 Monoclonal Antibodies

Male A/J mice (Harlan, Indianapolis, Ind.), 8-12 weeks old, were injected subcutaneously with 20 μg MT-IL13/Fc in complete Freund's adjuvant (Difco Laboratories, Detroit, Mich.) in 200 μL of PBS pH 7.4. At two-week intervals the mice were twice injected subcutaneously with 20 μg MT-IL13/Fc in incomplete Freund's adjuvant. Then, two weeks later and three days prior to sacrifice, the mice were again injected intraperitoneally with 20 μg of the same immunogen in PBS. Spleen cells isolated from one or more antigen-immunized mouse were used for fusion. Similar procedures of immunization and fusion were also used with *E. coli* expressed human IL13 (R&D Systems) as immunogen.

In the fusion leading to the generation of the anti-IL13 mAb 228B/C-1, $26.4 \times 10^6$ spleen cells and $58.8 \times 10^6$ spleen cells from two immunized mice were combined. For each fusion, single cell suspensions were prepared from the spleen of immunized mice and used for fusion with Sp2/0 myeloma cells. Sp2/0 and spleen cells at a ratio of 1:1 were fused in a medium containing 50% polyethylene glycol (M.W. 1450) (Kodak, Rochester, N.Y.) and 5% dimethylsulfoxide (Sigma). The cells were then adjusted to a concentration of $1.5 \times 10^5$ spleen cells per 250 μL of the suspension in DMEM medium (Invitrogen, Calif.), supplemented with 10% fetal bovine serum, 100 units/mL of penicillin, 100 μg/mL of streptomycin, 0.1 mM hypoxanthine, 0.4 μM aminopterin, and 16 μM thymidine. Two hundred and fifty microliters of the cell suspension were added to each well of about fifty 96-well microculture plates. After about ten days culture supernatants were withdrawn for screening for reactivity with MT-IL13/Fc in ELISA.

Wells of Immulon 2 (Dynatech Laboratories, Chantilly, Va.) microtest plates were coated by adding purified MT-IL13/Fc (0.1 μg/mL) overnight at room temperature. After the coating solution was removed by flicking of the plate, 200 μL of a blocking/diluting buffer (PBS containing 2% bovine serum albumin and 0.05% TWEEN® 20) was added to each well for one hour to block the non-specific sites. One hour later, the wells were then washed with PBST buffer (PBS containing 0.05% TWEEN® 20). Fifty microliters of culture supernatant was collected from each fusion well, mixed with 50 μL of the blocking/dilubng buffer and then added to the Individual wells of the microtest plates. After one hour of incubation, the wells were washed with PBST. The bound murine antibodies were then detected by reaction with HRP-conjugated goat anti-mouse IgG (Fc specific) (Jackson ImmunoResearch Lab, West Grove, Pa.) and diluted at 1:2, 000 with the blocking/diluting buffer. Peroxidase substrate solution containing 0.1% 3,3,5,5 tetramethyl benzidine (Sigma, St. Louis, Mo.) and 0.003% hydrogen peroxide (Sigma) was added to the wells for color development for 30 minutes. The reaction was terminated by the addition of 50 μL of 2 M $H_2SO_4$ per well. The $OD_{450}$ of the reaction mixture was measured with a BioTek ELISA Reader (BioTek Instruments, Winooski, V M).

The culture supernatants from the positive wells of MT-IL13/Fc screening were then tested for negative binding to an irrelevant Fy1 fusion protein. Final positive wells were then selected for single-cell cloning by limiting dilution. Culture supernatants from monoclonal antibodies were re-tested to confirm their reactivity by ELISA. Selected hybridomas were grown in spinner flasks and the spent culture supernatant collected for antibody purification by protein A affinity chromatography.

The purified antibodies were tested by four assays: i) Cross-reactivity with 293T cell expressed MT-IL13/Fc and *E. coli* expressed mouse IL13; ii) Inhibition of IL13-autocrine proliferation of HDLM-2 and L-1236 cells; iii) Inhibition of IL13-induced STAT6 phosphorylation in THP-1 cells; and iv) Inhibition of IL13-regulated CD14 and CD23 expression on human monocytes.

Seventy-three anti-IL13 mAbs were obtained from the fusions performed on MT-IL13/Fc and IL13 immunized mice. Thirty-nine of these mAbs were purified for characterization by ELISA and cell-based assays. Thirteen of these 39 mAbs inhibited autocrine IL13-induced proliferation of HDLM-2 and L-1236 cells (see assay description and results in Example 5). Four of the mAbs were found to be very strongly reactive with human IL13 in ELISA and were neutralizing against human IL13 in functional cell-based assays. These mAbs were designated 228B/C-1, 228A-4, 227-26, and 227-43. These antibodies were all generated using the glycosylated MT-IL13/Fc as immunogen.

Example 3

Reactivity of Anti-IL13 Monoclonal Antibodies with Human and Mouse IL13 in ELISA The reactivity of various anti-IL13 monoclonal antibodies was tested by ELISA. Different wells of 96-well microtest plates were coated with either *E. coli* expressed non-glycosylated human IL13 (R&D Systems), 293T cell expressed glycosylated MT-IL13/Fc, or *E. coli* expressed mouse IL13 (R&D Systems) by the addition of 100 μL of IL13 protein at 0.1 μg/mL in PBS. After overnight incubation at room temperature, the wells were treated with PBSTB (PBST containing 2% BSA) to saturate the remaining binding sites. The wells were then washed with PBST.

One hundred microliters of two-fold serially diluted anti-IL13 mAbs (0.5 μg/mL (3.33 nM) to 0.05 ng/mL (0.00033 nM)) were added to the wells for 1 hour at room temperature. An anti-IL13 mAb JES-5A2 from (BD Biosciences-Pharmingen, San Diego, Calif.) was also tested as a positive control, This antibody was generated by using *E. coli* expressed human IL13 as immunogen. An isotype-matched mouse anti-HIV-1 gp120 mAb was used as irrelevant negative control. The wells were then washed with PBST. Bound antibody was detected by incubation with diluted HRP-goat anti-mouse IgG (Fc) (Jackson ImmunoResearch) for 1 hour at room temperature. Peroxidase substrate solution was then added for color development as described above. The $OD_{450}$ was measured using an ELISA reader.

Figure 2:
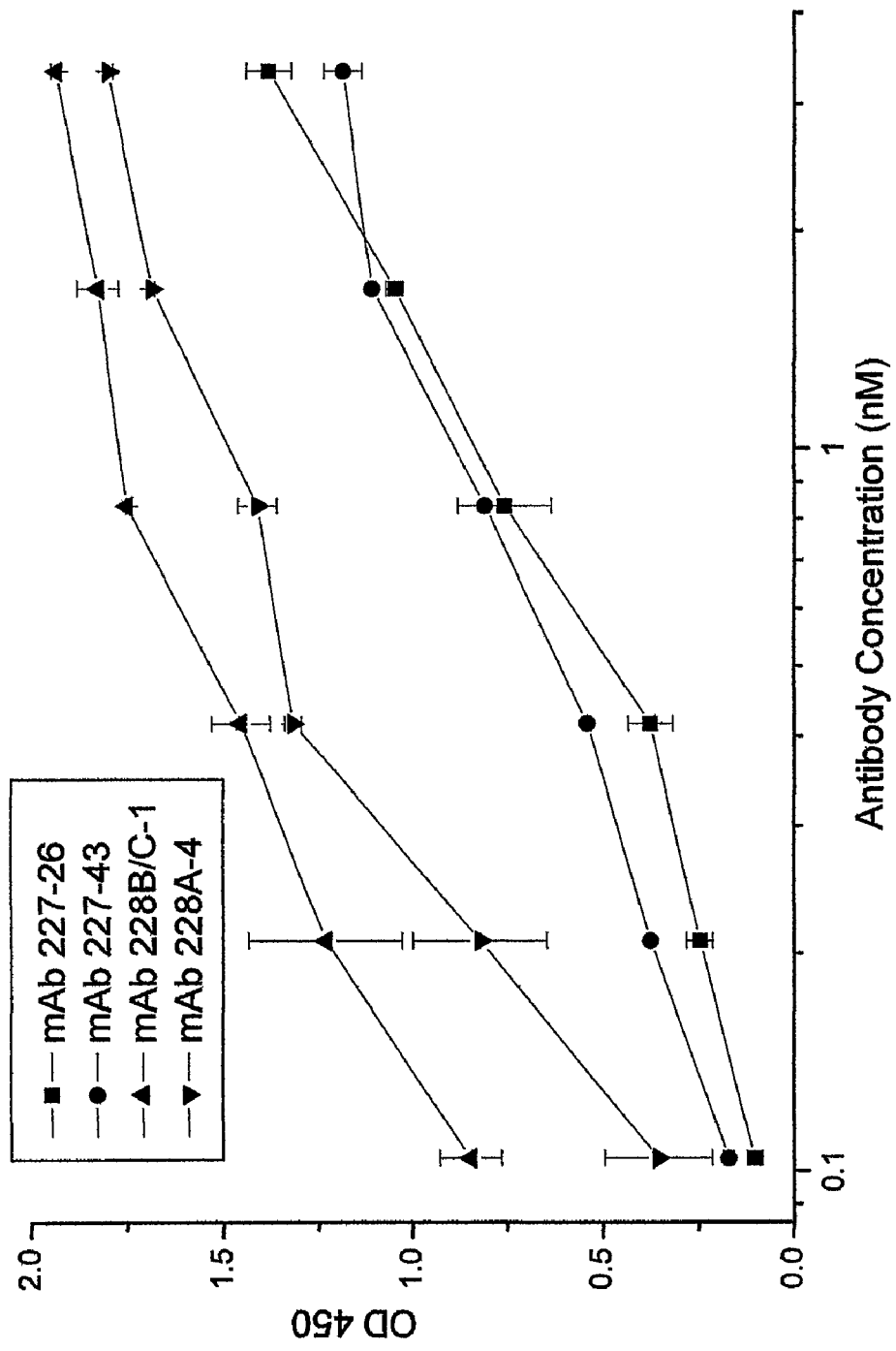
FIG. 2 depicts the binding of anti-IL13 monoclonal antibodies mutant IL13-Fc.

FIG. 1 shows the dose-dependent binding of anti-IL13 mAbs 228B/C-1, 228A-4, 227-26, 227-43, and the negative control in ELISA. Among these mAbs, 228B/C-1 showed the strongest reactivity. FIG. 2 shows the dose-dependent binding of the anti-IL13 mAbs to MT-IL13/Fc in ELISA. 228B8C-1 and 228A-4 showed the strongest reactivity with MT-IL13/Fc, whereas 227-26 and 227-43 showed moderate reactivity.

FIGS. 1 and 2 show that 228B/C-1 has highest affinity for both glycosylated and non-glycosylated human IL13 among all the anti-IL13 mAbs tested. All these anti-IL13 mAbs did not cross-react with mouse IL13 in ELISA (data no shown).

Example 4

Lack of Competition of 228B/C-1-HRP Binding to Human IL13 by JES10-5A2

To address whether JES10-5A2 and 228B/C-1 bind to the same epitope on human IL13, a competition ELISA was used to examine the effect of JES10-5A2 on 228B/C-1-HRP binding to *E. coli* expressed human IL13. Each well of 96-well microtest plates were incubated with 100 μL of IL13 protein at 0.1 μg/mL in PBS. After overnight incubation at room temperature, the wells were treated with PBSTB (PBST containing 2% BSA) to saturate the remaining binding sites. The wells were then washed with PBST. Fifty microliters of two fold serially diluted 228B/C-1 and JES10-5A2 (from a final concentration of 20 μg/mL to 9.76 ng/mL) were mixed with 50 µL of pre-titrated 228B/C-1-HRP (at 1:6,400 dilution). The mixtures were then added to the wells and incubated for 1 hour at room temperature. Peroxidase substrate solution was then added for color development as described above. The $OD_{450}$ was measured using an ELISA reader.

Figure 3:
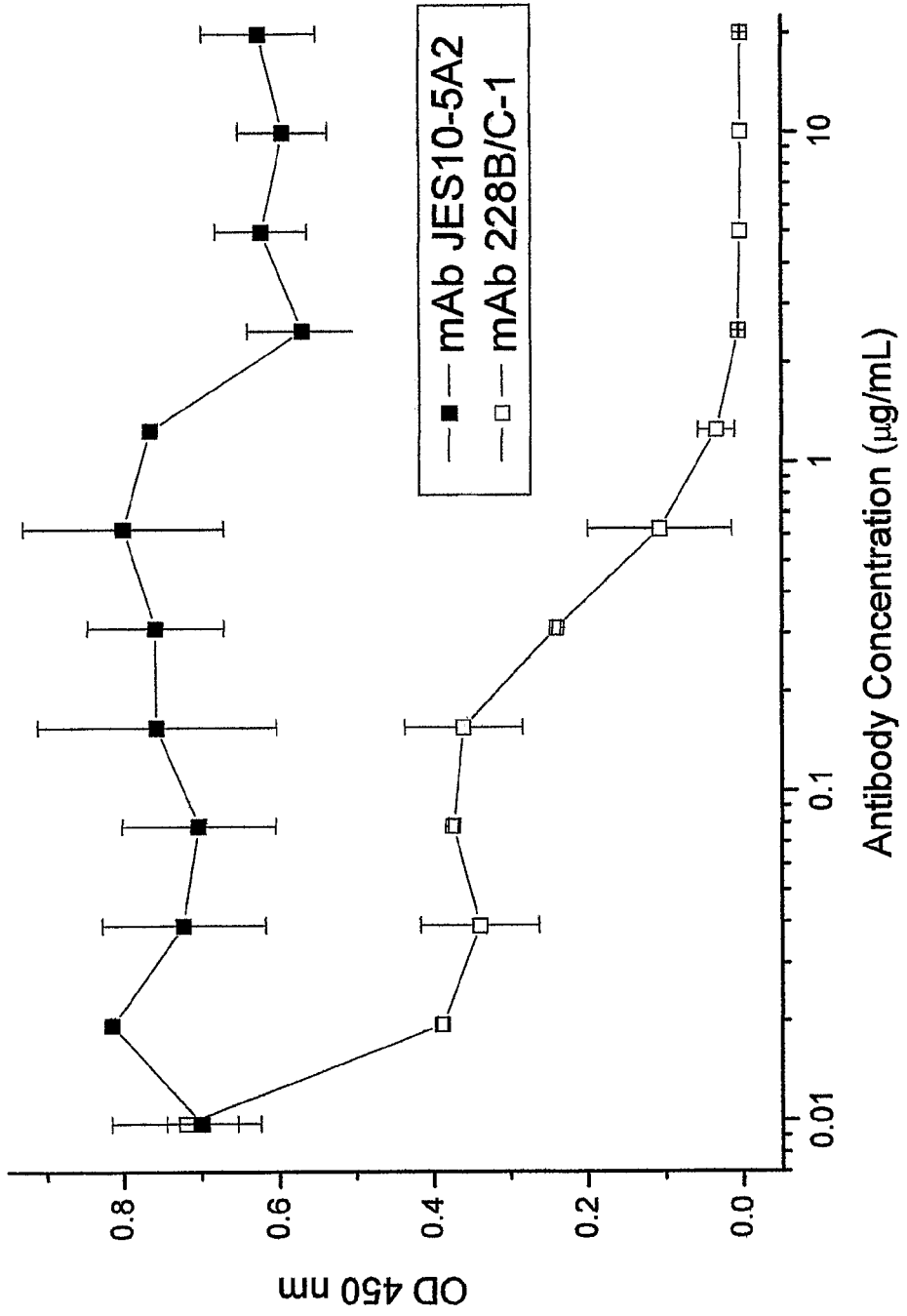
FIG. 3 illustrates that there is no inhibition of mAb 228B/C-1 binding to human IL13 by mAb JES10-5A2 (Pharmingen).

FIG. 3 demonstrates that JES10-5A2 does not compete with the binding of 228B/C-1-HRP to human IL13, indicating that 228B/C-1 and JES10-5A2 bind to different sites on human IL13.

Example 5

Screening for Anti-IL13 Neutralizing Monoclonal Antibodies by an IL-13-Autocrine Dependent Proliferation Assay Using L-1236 and HDLM-2 Cells L-1236 and HDLM-2 are Hodgkin lymphoma cell lines obtained from the German Collection of Microorganisms and Cell Cultures (DSMZ, Braunschweig, Germany). These cell lines produce IL13 which in turn activates their cell proliferation In an autocrine fashion (Kapp U et. al., J. Exp. Med. 189:1939 (1999)). Cells were cultured (25,000 cells/well) in the presence or absence of different anti-IL13 MAb (0.2, 0.02 and 0.002 µg/mL) in 5% $CO_2$ at 37° C. for 3-5 days. Cell proliferation was then measured either by an assay using the tetrazolium compound MTS (Promega, Madison, Wis.) (readouts at $OD_{490}$) or by the incorporation of $^3$H-thymidine (Amersham Biosciences, Piscataway, N.J.).

Figure 4:
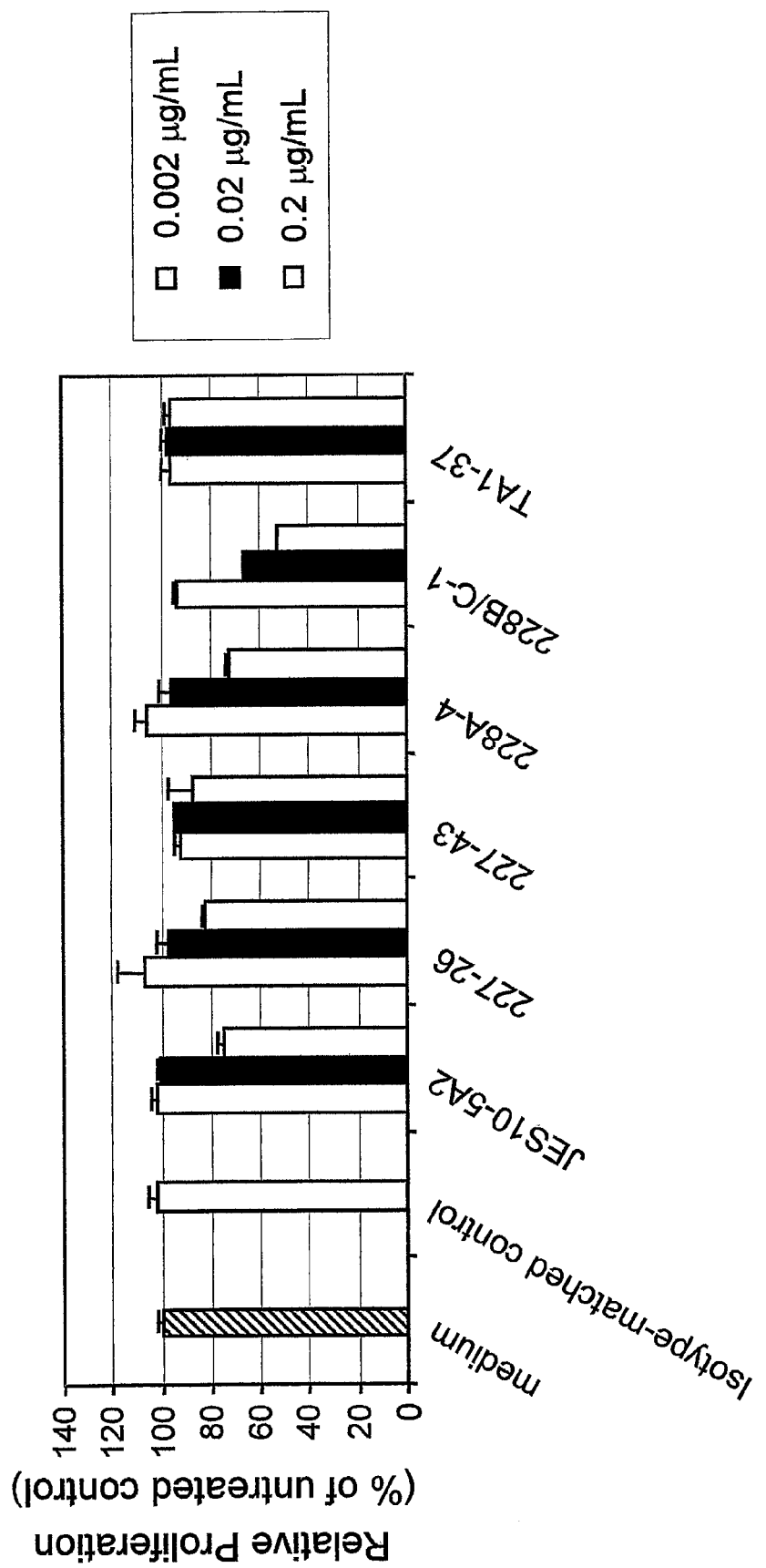
FIG. 4 illustrates the effect of anti-IL13 monoclonal antibodies on the proliferation of Hodgkin Lymphoma L-1236 cells.

The addition of an anti-IL13 neutralizing MAb to the culture of these cell lines was expected to inhibit their proliferation by the binding and inactivation of the IL13 produced by these cells. The results illustrated in FIG. 4 shows the effect of anti-IL13 mAb of the present invention on the proliferation of L-1235 cells. MAb 228B/C-1 displays the highest potency of inhibition of L-1236 cell proliferation in a dose-dependent manner among the neutralizing antibodies tested. TA1-37 (an anUi-IL13 MAb generated by using E. coli expressed human IL13 as immunogen) did not have any inhibitory activity even at a dose as high as 0.2 µg/mL. Similar results were obtained with HDLM-2 cells.

Example 6

Assay for IL13-Regulated CD14 and CD23 Expression on Primary Human Monocytes

IL13 induces suppression of CD14 expression and the up-regulation of CD23 expression in the human monocytes (de Waal Malefyt et al., J. Immunol., 151: 6370 (1993), Chomarat et al., Int. Rev. Immunol., 17:1 (1998)). Peripheral blood leukocytes (PBLS) were isolated from freshly collected, heparinized whole blood of healthy human donors by density-gradient centrifugation in Histopaque-1077 (Sigma). PBLs ($1.5 \times 10^6$) suspended in RPMI-1640 medium (Invitrogen) with 5% fetal bovine serum were added to each well of a 96-well tissue culture plate containing recombinant IL13 (final 10 ng/mL=0.813 nM) and an anti-IL13 monoclonal antibody or an irrelevant antibody (three-fold serial dilutions, from a final 12 µg/mL=80 nM). CD14 expression or CD23 expression on monocytes was suppressed or up-regulated, respectively, by the addition of 0.813 nM human IL13 to the incubating medium. The medium control contained RPMI-1640/FBS medium without recombinant IL13.

The cells were incubated in 5% $CO_2$ at 37° C. for 2 days. The cells were harvested for staining with anti-CD14-FITC or anti-CD23-PE (BD Biosciences-Pharmingen). The expression levels of CD14 and CD23 in the monocyte population were measured by flow cytometry and represented by Median Fluorescence Intensity (MFI).

Figure 5:
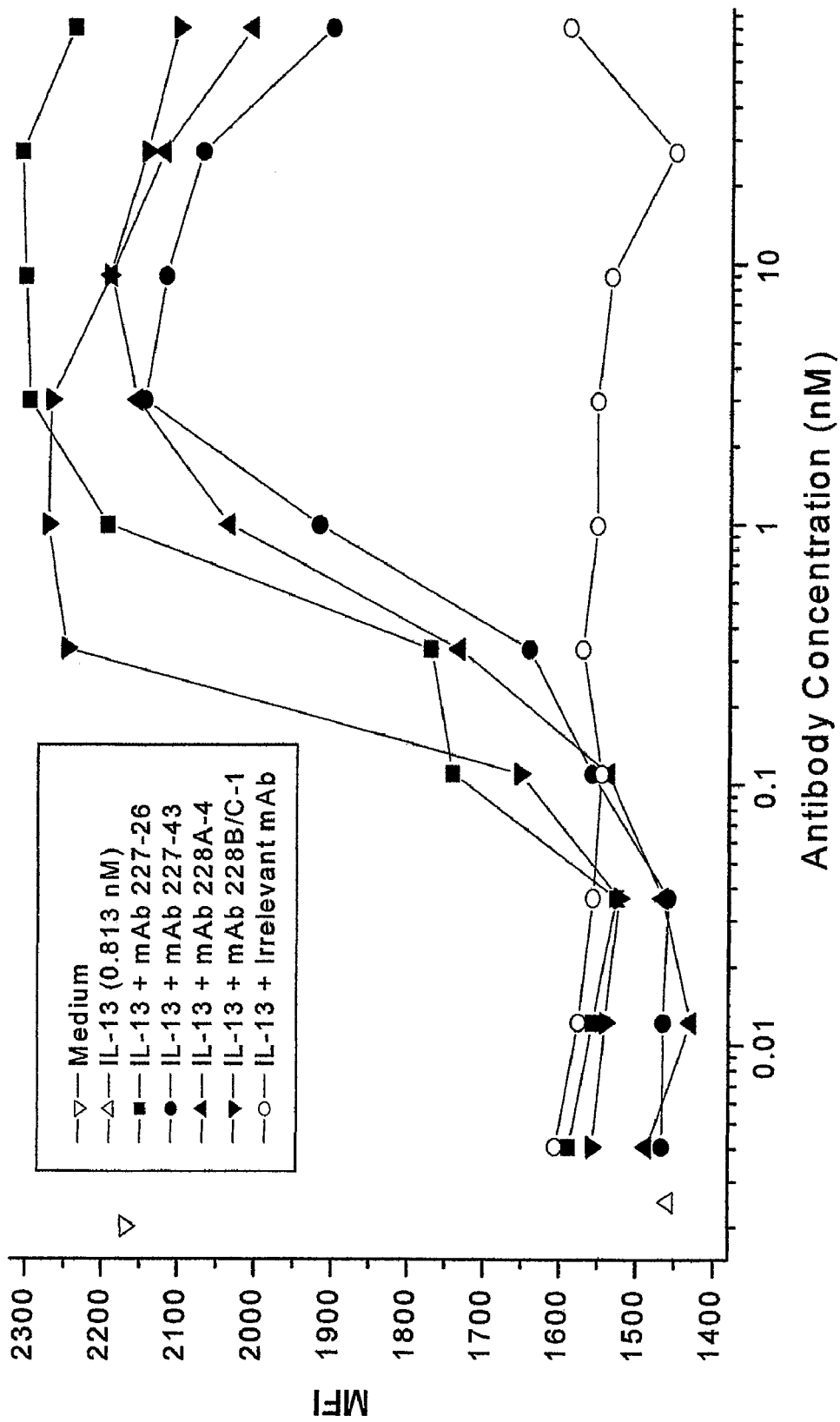
FIG. 5 illustrates the effect of anti-IL13 monoclonal antibodies on IL13-induced suppression of CD14 expression in human monocytes.

The effects of anti-IL13 MAbs on IL13-suppressed CD14 expression on human monocytes are depicted in FIG. 5. Among all the anti-IL13 MAbs tested, 228B/C-1 had the highest potency in inhibiting the effect of IL13 on CD14 expression. Complete inhibition of the effect of IL13 was achieved at 0.33 nM. The inhibitory activities of MAbs 227-26 and 228A-4 were moderate, whereas that of JES10-5A2 was weak. The effect of IL13 could not be completely inhibited by JES10-5A2 even at 80 nM.

Figure 6:
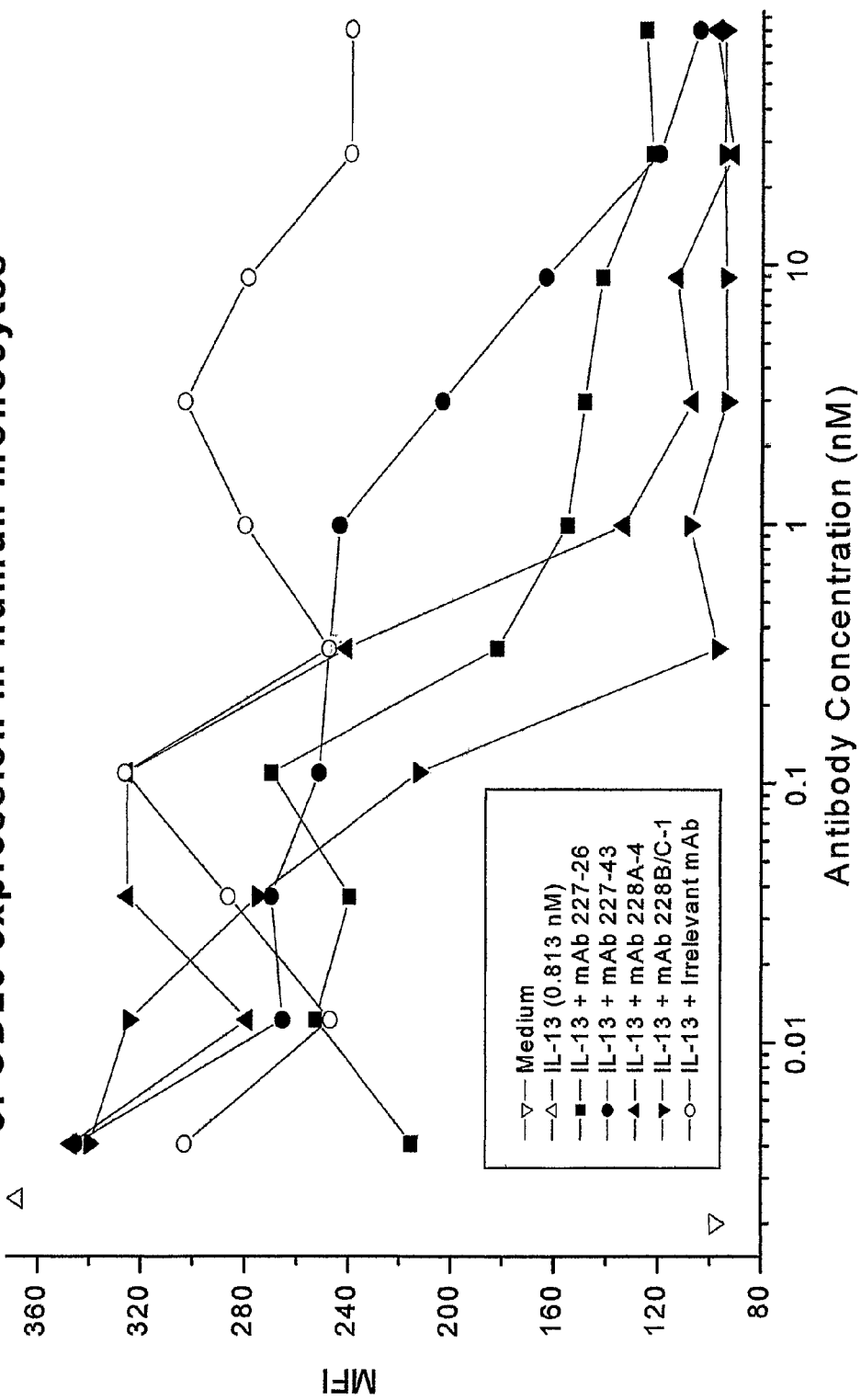
FIG. 6 illustrates the effect of anti-IL13 monoclonal antibodies on IL13-induced up-regulation of CD23 expression in human monocytes.

The effects of anti-IL13 MAbs on IL13-induced CD23 up-regulation on human monocytes are depicted in FIG. 6. Similar to the results on CD14 expression (FIG. 5), 228B/C-1 was most potent in inhibiting the effect of IL13 on CD23 expression among the anti-IL13 MAbs tested. Complete inhibition by 228B/C-1 was achieved at 0.33 nM. The inhibitory potency of JES10-5A2 was weak.

Based on the results presented in FIGS. 5 and 6, complete inhibition of IL13 by 228B/C-1 can be achieved at a molar stoichiometric ratio of 1:2 (mAb:IL13), and, therefore, 228B/C-1 is a very high affinity neutralizing MAb against human IL13.

Example 7

IL13-Induced STAT6 Phosphorylation Assay in THP-1 Cells

IL13 can activate the myeloid cell line THP-1 (ATCC, Manassas, Va.) to induce phosphorylation of STAT6 which is a critical step in the signal transduction pathway of IL13 (Murata T et al., Int. Immunol. 10: 1103-1110 (1998). The anti-IL13 MAbs were tested for inhibition of IL13 in this assay.

THP-1 cells were maintained in Dulbecco's Modified Eagle Medium (DMEM) (Invitrogen) supplemented with 5% fetal bovine serum. On the day of experiments, the cells were washed and incubated in serum-free DMEM at 37° C. in 5% $CO_2$ for 2 hours. $0.3 \times 10^6$ cells in 80 µL of the serum-free medium were then added to each well of a 96-well round-bottom plate. One hundred and twenty microliters of medium containing human IL13 (final concentration of 10 ng/mL=0.813 nM) and anti-IL13 MAbs (5 fold serial dilutions, from final concentration of 0.5 µg/mL=3.333 nM). Negative control wells containing either no IL13 or IL13 and an isotype-matched irrelevant mouse MAb.

The mixtures were incubated at 37° C. under 5% $CO_2$ for 10 min. The plates were then centrifuged at 300×g for 3 minutes at 4° C. After discarding the supernatant, the cell pellets were resuspended in 100 µL of Laemmli non-reducing sample buffer (SDS-PAGE loading buffer, BioRad, CA) and then transferred to microcentrifuge tubes. The tubes were heated at 95° C. for 5 minutes and then centrifuged at 10,000×g for 10 minutes at room temperature. The supernatants were collected and analyzed by 4-20% gradient SDS-PAGE. The separated proteins were transferred to PVDF membrane which was then incubated with diluted mouse anti-human Stat6 (Y641, phospho-specific) mAb (BD Biosciences Pharmingen).

Figure 7:
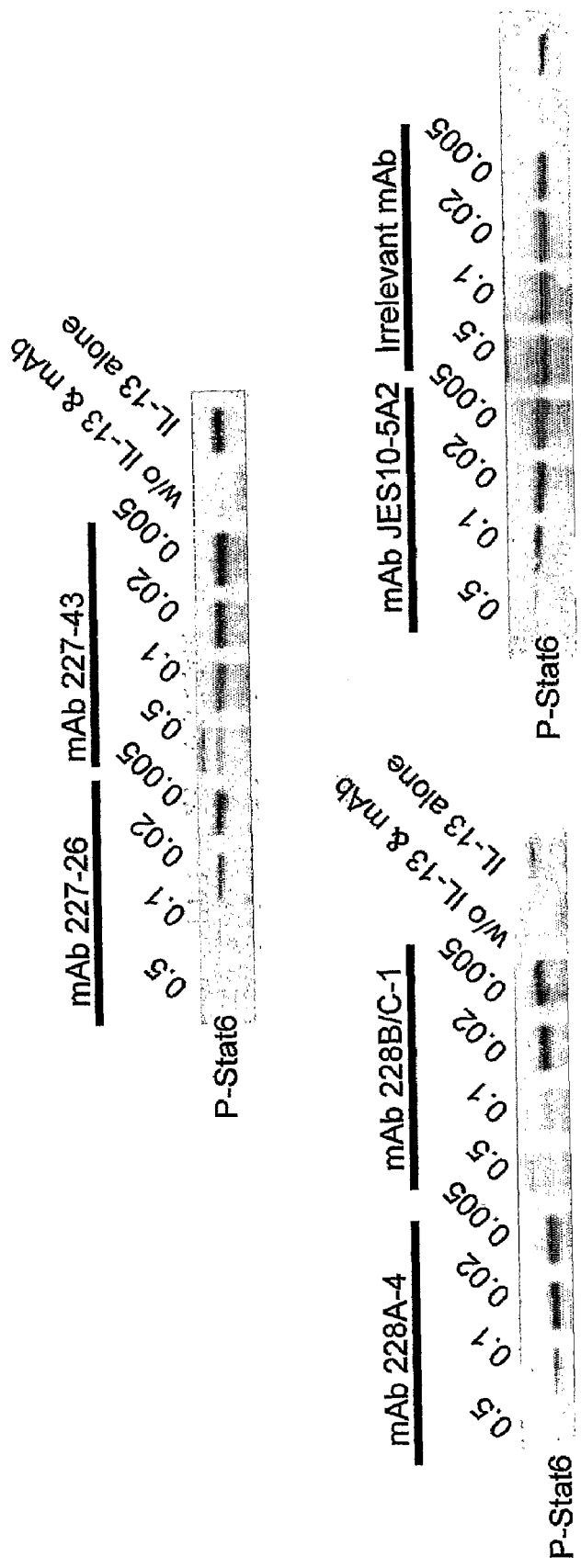
FIG. 7 illustrates the effect of anti-IL13 monoclonal antibodies on IL13-induced STAT6 phosphorylation in THP-1 cells.

The bound antibody was detected by HRP conjugated goat anti-mouse IgG (Fc) antibodies (Jackson ImmunoResearch Laboratories). The immunoreactive proteins were identified on film, using enhanced chemiluminescence detection (Supersignal West Pico Chemiluminescent Substrate, Pierce) FIG. 7 depicts the results of the effect of anti-IL13 MAbs on IL13-induced phosphorylation of Stat6 in THP-1 cells. Stat6 is phosphorylated in THP-1 cells treated with 0.813 nM human IL13. Dose-dependent inhibition of Stat6 phosphorylation was found when the cells were treated with MAbs 228B/C-1, 228A4, 227-26, 227-43 and JES10-5A2. MAb 228B/C-1 is the most potent neutralizing antibodies among the anti-IL13 mAbs tested. Complete inhibition by 228B/C-1 was achieved at a concentration between 0.667 nM and 0.133 nM. The approximate molar stoichiometric ratio between 228B/C1 and IL13 for complete inhibition was 1:2. It is consistent with the data shown in FIGS. 5 and 6.

Example 8

Example 8

Molecular Cloning of Heavy and Light Chain Genes Encoding Anti-IL13 Monoclonal Antibodies Total RNA was isolated from hybridoma cells using a QIAGEN kit (Valencia, Calif.). Reverse transcription (first strand cDNA) reaction was carried out as follows: 1-1.5 mg of total RNA was mixed with 1 ml 10 mM dNTPs, 50 ng random Hexamers, and RNase free water in a final volume of 12 mL.

The reaction mixture was incubated at 65° C. for 5 minutes and placed on ice immediately for 1 minute. After a brief centrifugation, the following reagents were added: 4 mL of 5× first strand buffer (250 mM Tris-HCl, pH 8.3, 375 mM KCl, 15 mM $MgCl_2$), 2 mL of 0.1 mM DTT, and 1 mL of RNase-OUT RNase inhibitor (40 U/mL). After mixing, the reaction was incubated at room temperature for 2 minutes. One milliliter of Superscript II RT (50 U/ml) was then added to the mixture for incubation at 25° C. for 10 minutes followed by 50 minutes at 42° C. After a brief centrifugation, the reaction was incubated for 15 minutes at 70° C. to inactivate the reverse transcriptase. One microliter of RNase H (2 U/ml) was then added and the reaction was incubated for 20 minutes at 37° C. to destroy RNA.

To amplify the variable regions of the heavy and light chains, a method described by O'Brien and Jones (O'Brien S. and Jones T., "Humanizing antibodies by CDR grafting", Antibody Engineering, Springer Lab manual, Eds. Kontermann and Duble, S (2001)) was used. Briefly, 5' primers were selected from the signal peptide region (11 sets for light chain and 12 sets of degenerate primers for heavy chain) and 3' primers were selected from the constant region of either the light or heavy chain. 5' and 3' primers (1.5 mL of 10 mM) were mixed with 5 mL of 10×PCR buffer (250 mM Tris-HCl, pH 8.8, 20 mM $MgSO_4$, 100 mM KCl, 100 mM $(NH_4)_2 SO_4$, 1% Triton X-100, 1 mg/mL nuclease free BSA), 1 mL cDNA as prepared previously, 1 mL of Turbo pfu (Stratagene) and water to adjust the total volume of the reaction to 50 mL. PCR was performed as follows: 1 cycle at 94° C. for 4 minutes; 25 cycles at 94° C. for 30 seconds, at 53° C. for 30 seconds, and at 72° C. for 45 seconds; and 1 cycle at 72° C. for 7 minutes. Reaction mixtures were resolved by electrophoresis in a 1% agarose gel.

Amplified DNA fragment was purified and cloned into a pcDNA3.1 vector. Cloning was carried out using the Invitrogen TOPO cloning kit following the manufacturer's suggested protocol (Invitrogen). Fifteen to twenty colonies of transformed E. coli were used for plasmid purification. Plasmids were sequenced using a T7 primer. The predominant sequences for the heavy and light chains were cloned into an M13 Fab expression vector by hybridization mutagenesis (Glaser S. et al. Antibody Engineering (Oxford University Press, New York (1995)), Near RI, BioTechniques 12: 88 (1992)). Binding properties of the expressed Fab were confirmed by ELISA. FIG. 8 depicts the VH and VL chain amino acid sequences for 228B/C.

Example 9

Epitope Mapping

Anti-IL13 MAb 228B/C1 binds to a conformational epitope and binds to cynomologous monkey IL13 with the same high affinity as it does to human IL13. However, 228B/C does not bind to murine IL13. So, the strategy devised for epitope mapping was to exchange small portions of the monkey IL13 with the corresponding mouse IL13 sequence. Overlapping oligonucleotides were synthesized. Two rounds of PCR were performed to assemble the IL13 hybrid constructs so that part of monkey IL13 was replaced by the corresponding sequence from mouse IL13. The final PCR amplified IL13 coding regions were cloned into pcDNA3.1 vector in frame with a V5 tag using TOPO cloning kit (Invitrogen). All PCR amplified region were confirmed by sequencing to contain only the desired domain swapping mutations and not additional unwanted mutation in the expression vectors.

The anti-IL13 MAb binding epitope was identified as a 8-mer peptide from amino acid #49 to 56, ESLINVSG (SEQ ID NO 18). This epitope is located in Helix-B and loop-BC in human IL13. When the epitope peptide derived from cyno-IL13 was used to swap the corresponding sequence in murine IL13, the resulting hybrid IL13 molecule can bind to 228B/C with affinity similar to that of the original cynoIL13, further validated that 228B/C MAb binding to cyno or human IL13 at this peptide between residual #49-56. Sequence comparison between human, cyno, and murine IL13 reveals only three residues Ile52, Val54, Gly56 in human IL13 are not conserved, suggesting the critical residues for IL13 and anti-IL13 MAb interaction through this 8-mer peptide Is determined by one or combination of some of these three residues.

This epitope was further confirmed by peptide spot analysis. The entire human IL13 peptide was scanned with a series of overlapping 12-mer peptides synthesized via SPOT on cellulose membrane. The only anti-IL13 MAb reactive peptide was identified as a 12-mer peptide of amino acid #44-56, YCAALESLINVS (SEQ ID NO 19), which is overlapping with the region identified through domain swapping experiments.

Example 10

ADCC Assay for Anti-IL-13 MAb

PBMCs are isolated from fresh heparinized blood samples by standard centrifugation techniques using Ficoll-paque (50 ml buffy coat gives ~300×$10^6$ PBMCs). The PBMCs are stimulated (20×$10^6$ PBMC) with IL-2 (10 U/ml) in RPMI1640/10% FCS for 24 hrs at 37° C., 5% $CO_2$.

After 24 hrs, HDLM-2 or L-1236 (Hodgkin's lymphoma cell lines) target cells (2×$10^6$ cells) are labelled by incubating with 400 uCi of $^{51}Cr$ (sodium chromate) overnight at 37° C. $^{51}Cr$-labeled cells are washed 4× and resuspended in RPM11640/5% FCS. The labeled cells are then aliquoted into 96-well U-bottom plates (duplicate well). The IL-2 stimulated PBMCs are then added at different E:T ratio (e.g. 80:1, 20:1).

The anti-IL13 Mabs to be tested are serially diluted and aliquoted into wells so that the final MAb concentration is between, e.g., 0, 0.5, 5, 50 ug/ml. After incubation, the plates are centrifuged at 900 rpm for 3 minutes. The supernatant from each well is collected and the amount of radioactivity counted. The percent cell lysis is calculated according to the following equation:

% cell lysis=(Cpm$_{test}$−Cpm$_{spont}$)/ (Cpm$_{max}$−Cpm$_{spont}$)×100%

[For additional ADCC information, see, e.g., L. M. Weiner et at, Cancer Res., 48:2568-2573 (1988); P. Hersey et at, Cancer Res., 46:6083-6090 (1988); and C. J. Hansik et at, Proc. Natl. Acad. Sci., 83:7893-97 (1986)].

Example 11

Assay of Complement-Mediated Cytotoxicity (CMC)

Tumor cells (5×10$^4$ in 50 μL of DMEM culture medium), normal human serum (1:1 dilution in 50 μL of medium), and various concentrations of humanized anti-IL13 MAb (IgG1) (in 100 μL of medium) may be incubated in 96-well flat-bottomed plates for 2 hours at 37° C. in 5% $CO_2$. An irrelevant isotype-matched antibody may be used as negative control. A cell-proliferation reagent WST-1 (15 μL; Roche Diagnostics, Basel, Switzerland) is added and incubated for 5 hours at 37° C. Optical density of the color reaction is read at 450 nm with an ELISA plate reader. Percent inhibition of CMC by the anti-IL13 MAb=100×(OD$_{s/a}$−OD$_s$)/(OD$_{ns}$−OD$_s$); OD$_{s/a}$= OD for wells treated with serum and antibody; OD$_s$=OD for wells treated with serum; OD$_{ns}$=OD for wells treated without serum and antibody.

Deposits

The following cultures have been deposited with the American Type Culture Collection, 10801 University Boulevard. Manassas Va. 20110-2209 USA (ATCC):

| Hybridoma | ATCC NO. | Deposit Date |
| --- | --- | --- |
| Anti-IL13 228B/C-1 | PTA-5657 | Nov. 20, 2003 |
| Anti-IL13 228A-4 | PTA-5656 | Nov. 20, 2003 |
| Anti-IL13 227-26 | PTA-5654 | Nov. 20, 2003 |
| Anti-IL13 227-43 | PTA-5655 | Nov. 20, 2003 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, which assures permanent and unrestricted availability of the progeny of the culture to the public upon issuance of the pertinent U.S. patent.

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as illustration of one aspect of the invention and any culture that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating cancer in a patient, comprising administering to a patient in need thereof an effective amount of an anti-IL-13 antibody or an antigen binding fragment thereof that binds specifically to human IL-13, wherein said antibody or antigen binding fragment thereof competes with an antibody produced by hybridoma 228B/C-1 having ATCC Accession No. PTA-5657.

2. The method of claim 1, wherein the anti-IL-13 antibody or antigen-binding fragment binds an epitope having the amino acid sequence ESLINVSG (SEQ ID NO:18) or YCAALESIANVS (SEQ ID NO:19).

3. The method of claim 1 or 2, wherein the anti-IL-13 antibody or antigen-binding fragment comprises a light chain comprising a CDRL1 having the amino acid sequence of SEQ ID NO: 99, a CDRL2 having the amino acid sequence of SEQ ID NO:104; and a CDRL3 having the amino acid sequence of SEQ ID NO: 115.

4. The method of claim 1 or 2, wherein the anti-IL-13 antibody or antigen-binding fragment comprises a heavy chain comprising a CDRH1 having the amino acid sequence of SEQ ID NO: 117, a CDRH2 having the amino acid sequence of SEQ ID NO: 123; and a CDRH3 having the amino acid sequence of SEQ ID NO: 135.

5. The method of claim 4, wherein the anti-IL-13 antibody or antigen-binding fragment comprises a light chain comprising a CDRL1 having the amino acid sequence of SEQ ID NO: 99, a CDRL2 having the amino acid sequence of SEQ ID NO:104; and a CDRL3 having the amino acid sequence of SEQ ID NO: 115.

6. The method of claim 1 or 2, wherein the anti-IL-13 antibody or antigen-binding fragment comprises a light chain comprising the amino acid sequence of SEQ ID NO: 3, 142, 144 or 150; and a heavy chain comprising the amino acid sequence of SEQ ID NO: 4, 143, 145, 146, 147, 148 or 149.

7. The method of claim 1 or 2, wherein the anti-IL-13 antibody or antigen-binding fragment comprises the amino acid sequence of SEQ ID NO: 142 or 143.

8. The method of claim 1 or 2, wherein the anti-IL-13 antibody or antigen-binding fragment comprises a light chain comprising the amino acid sequence of SEQ ID NO: 142, and a heavy chain comprising the amino acid sequence of SEQ ID NO: 143.

9. The method of claim 1 or 2, wherein the anti-IL-13 antibody or antigen-binding fragment comprises a heavy chain comprising:
   (a) a CDRH1 having the amino acid sequence SEQ ID NO: 117, 118, 119, 120, 121 or 122;
   (b) a CDRH2 having the amino acid sequence SEQ ID NO: 123, 124, 125, 126, 127, 128, 129, 130, 131, 132, 133 or 134; and
   (c) a CDRH3 having the amino acid sequence SEQ ID NO: 135, 136, 137, 138, 139, 140 or 141.

10. The method of claim 1 or 2 wherein the anti-IL-13 antibody or antigen-binding fragment comprises a light chain comprising:
   (a) a CDRL1 having the amino acid sequence SEQ ID NO: 99, 100, 101, 102 or 103;
   (b) a CDRL2 having the amino acid sequence SEQ ID NO: 104, 105, 106, 107, 108, 109, 110, 111, 112, 113, or 114; and
   (c) a CDRL3 having the amino acid sequence of SEQ ID NO: 115 or 116.

11. The method of claim 1 or 2, wherein the anti-IL-13 antibody or antigen-binding fragment is a monoclonal antibody.

12. The method of claim 1 or 2, wherein the anti-IL-13 antibody or antigen-binding fragment is an IgG antibody or a fragment thereof.

13. The method of claim 12, wherein the anti-IL-13 antibody or antigen-binding fragment is an IgG1, an IgG2, an IgG3 or an IgG4 antibody or a fragment thereof.

14. The method of claim 1 or 2, wherein the anti-IL-13 antibody or antigen-binding fragment is a human antibody, a chimeric antibody or a humanized antibody or a fragment thereof.

15. The method of claim 1 or 2, wherein the anti-IL-13 antibody or antigen-binding fragment is a single chain antibody.

16. The method of claim 1 or 2, wherein the anti-IL-13 antibody mediates tumor cell killing by antibody dependent cell-mediated cytotoxicity and/or complement mediated cytotoxicity.

17. The method of claim 1 or 2, wherein the anti-IL-13 antibody or antigen binding fragment is administered by inhalation, bolus injection, or infusion.

18. The method of claim 1 or 2, wherein said cancer is Hodgkin's disease, skin cancer, stomach cancer, colon cancer, breast cancer, pancreatic cancer, liver cancer, prostate cancer, lung cancer, head-and-neck cancer, renal cell cancer, squamous cell carcinoma, AIDS-associated Kaposi's carcinoma or brain cancer.

19. The method of claim 1 or 2, wherein the anti-IL-13 antibody is associated with a cytotoxic agent.

20. The method of claim 19, wherein the cytotoxic agent is a radioisotope or a chemotherapeutic agent.

21. A method of diagnosing a cancer or tumor that overexpresses IL-13 in a biological sample, comprising detecting overexpression of IL-13 in the biological sample taken from a patient suspected of having said cancer or tumor by contacting the biological sample with an anti-IL-13 antibody or antigen-binding fragment thereof that binds specifically to human IL-13, wherein said antibody competes with an antibody produced by hybridoma 228B/C-1 having ATCC Accession No. PTA-5657 for binding to IL-13.

22. The method of claim 21, wherein the anti-IL-13 antibody or antigen-binding fragment binds an epitope having the amino acid sequence ESLINVSG (SEQ ID NO:18) or YCAALESLINVS (SEQ ID NO:19).

23. The method of claim 21 or 22, wherein the anti-IL-13 antibody or antigen-binding fragment comprises a light chain comprising a CDRL1 having the amino acid sequence of SEQ ID NO: 99, a CDRL2 having the amino acid sequence of SEQ ID NO: 104; and a CDRL3 having the amino acid sequence of SEQ ID NO: 115.

24. The method of claim 21 or 22, wherein the anti-IL-13 antibody or antigen-binding fragment comprises a heavy chain comprising a CDRH1 having the amino acid sequence of SEQ ID NO: 117, a CDRH2 having the amino acid sequence of SEQ ID NO: 123, and a CDRH3 having the amino acid sequence of SEQ ID NO: 135.

25. The method of claim 24, wherein the anti-IL-13 antibody or antigen-binding fragment comprises a light chain comprising a CDRL1 having the amino acid sequence of SEQ ID NO: 99, a CDRL2 having the amino acid sequence of SEQ ID NO: 104; and a CDRL3 having the amino acid sequence of SEQ ID NO: 115.

26. The method of claim 21 or 22, wherein the anti-IL-13 antibody or antigen-binding fragment comprises a light chain comprising the amino acid sequence of SEQ ID NO: 3, 142, 144 or 150; and said antibody comprises a heavy chain comprising the amino acid sequence of SEQ ID NO: 4, 143, 145, 146, 147, 148 or 149.

27. The method of claim 21 or 22, wherein the anti-IL-13 antibody or antigen-binding fragment comprises the amino acid sequence of SEQ ID NO: 142 or 143.

28. The method of claim 21 or 22, wherein the anti-IL-13 antibody or antigen-binding fragment comprises a light chain comprising the amino acid sequence of SEQ ID NO: 142, and a heavy chain comprising the amino acid sequence of SEQ ID NO: 143.

29. The method of claim 21 or 22, wherein the anti-IL-13 antibody or antigen-binding fragment is a human antibody, a chimeric antibody or a humanized antibody or a fragment thereof.

30. The method of claim 29, wherein said cancer is Hodgkin's disease, skin cancer, stomach cancer, colon cancer, breast cancer, pancreatic cancer, liver cancer, prostate cancer, lung cancer, head-and-neck cancer, renal cell cancer, squamous cell carcinoma, AIDS-associated Kaposi's carcinoma or brain cancer.

* * * * *

UNITED STATES PATENT AND TRADEMARK OFFICE
CERTIFICATE OF CORRECTION

PATENT NO.       : 7,674,459 B2                                     Page 1 of 1
APPLICATION NO.  : 10/583926
DATED            : March 9, 2010
INVENTOR(S)      : Fung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this
Eleventh Day of January, 2011

David J. Kappos
*Director of the United States Patent and Trademark Office*

UNITED STATES PATENT AND TRADEMARK OFFICE
CERTIFICATE OF CORRECTION

PATENT NO.        : 7,674,459 B2
APPLICATION NO.   : 10/583926
DATED             : March 9, 2010
INVENTOR(S)       : Sek Chung Fung et al.

Page 1 of 1

It is certified that error appears in the above-identified patent and that said Letters Patent is hereby corrected as shown below:

In the Claims:

Column 105 at claim number 2, line 12, please replace "YCAALESIANVS (SEQ ID NO:19)" with --YCAALESLINVS (SEQ ID No:19)--.

Signed and Sealed this
Tenth Day of March, 2015

Michelle K. Lee
*Deputy Director of the United States Patent and Trademark Office*